(12) United States Patent
Gregory et al.

(10) Patent No.: US 12,405,238 B2
(45) Date of Patent: Sep. 2, 2025

(54) ULTRASENSITIVE, ULTRATHIN VAPOR SENSORS AND ARRAYS

(71) Applicant: Trace Sensing Technologies Inc., Wallingford, CT (US)

(72) Inventors: Otto J. Gregory, Narragansett, RI (US); Peter P. Ricci, West Warwick, RI (US)

(73) Assignee: Trace Sensing Technologies Inc., Wallingford, CT (US)

( * ) Notice: Subject to any disclaimer, the term of this patent is extended or adjusted under 35 U.S.C. 154(b) by 806 days.

(21) Appl. No.: 17/659,909

(22) Filed: Apr. 20, 2022

(65) Prior Publication Data

US 2022/0412905 A1    Dec. 29, 2022

Related U.S. Application Data

(63) Continuation-in-part of application No. 17/356,392, filed on Jun. 23, 2021, now Pat. No. 11,340,183.

(51) Int. Cl.
*G01N 25/48* (2006.01)
*A61B 5/00* (2006.01)
*G01N 33/497* (2006.01)

(52) U.S. Cl.
CPC ......... *G01N 25/488* (2013.01); *A61B 5/6833* (2013.01); *G01N 33/4975* (2024.05)

(58) Field of Classification Search
CPC ............ G01N 25/488; G01N 33/4975; G01N 25/4893; G01N 27/14; G01N 33/0031; A61B 5/6833

See application file for complete search history.

(56) References Cited

U.S. PATENT DOCUMENTS

| | | |
|---|---|---|
| 4,030,340 A | 6/1977 | Chang |
| 4,542,640 A | 9/1985 | Clifford |

(Continued)

FOREIGN PATENT DOCUMENTS

| | | |
|---|---|---|
| DE | 4334410 A1 | 4/1995 |
| EP | 0750192 A2 | 12/1996 |

(Continued)

OTHER PUBLICATIONS

Aguilar, et al., A Hybrid Nanosensor for TNT Vapor Detection, Nano Letters, 10(2):380-384 (Feb. 2010).

(Continued)

*Primary Examiner* — Robert G Bachner
(74) *Attorney, Agent, or Firm* — Greenberg Traurig, LLP; Christopher C. Bolten

(57) ABSTRACT

Ultrasensitive, ultrathin thermodynamic sensing platforms for the detection of chemical compounds at trace levels are disclosed. Embodiments of the ultrathin sensor comprise substrate, adhesion, microheater, and catalyst layers. A sensor array may include a plurality of sensors each having a different catalyst. When a sensor array exposed to an analyte, each of the various sensors of the array may experience an endothermic reaction, an exothermic reaction, or no reaction. A comparison of the reaction results to data comprising previously-obtained reaction results may be used to determine information on the analyte. Advantageously, these ultrathin vapor sensors utilize less power and provide greater sensitivity, and may be used to detect and identify analytes at the PPT level. Specialized sensors configured to detect analytes falling into a certain category (e.g., explosives, drugs and narcotics, biomarkers, etc.) are disclosed, as well as general purpose sensors capable of detecting analytes from a plurality of categories.

21 Claims, 22 Drawing Sheets

(56) References Cited

U.S. PATENT DOCUMENTS

| | | |
|---|---|---|
| 5,137,924 A | 8/1992 | Short et al. |
| 5,501,297 A | 3/1996 | Josephs |
| 5,541,851 A | 7/1996 | Sato et al. |
| 5,731,510 A | 3/1998 | Jones et al. |
| 5,997,832 A | 12/1999 | Lieber et al. |
| 6,171,378 B1 | 1/2001 | Manginell et al. |
| 7,147,695 B2 | 12/2006 | Mitra |
| 7,329,389 B2 | 2/2008 | Horovitz et al. |
| 7,581,434 B1 | 9/2009 | Discenzo et al. |
| 7,611,671 B2 | 11/2009 | Anvar et al. |
| 8,216,398 B2 | 7/2012 | Bledsoe et al. |
| 9,304,102 B2 | 4/2016 | Day et al. |
| 9,518,970 B2 | 12/2016 | Burgi et al. |
| 9,678,030 B2 | 6/2017 | Potyrailo et al. |
| 9,759,699 B1 | 9/2017 | Gregory et al. |
| 10,272,434 B2 | 4/2019 | Khattak et al. |
| 10,330,624 B2 | 6/2019 | Tayebi et al. |
| 10,416,140 B2 | 9/2019 | Von Waldkirch |
| 11,041,838 B2 | 6/2021 | Rogers et al. |
| 2001/0003249 A1 | 6/2001 | Stormbom |
| 2004/0241870 A1 | 12/2004 | Miller et al. |
| 2005/0011260 A1 | 1/2005 | Arndt et al. |
| 2005/0109621 A1 | 5/2005 | Hauser et al. |
| 2005/0260453 A1 | 11/2005 | Jiao et al. |
| 2006/0254501 A1 | 11/2006 | Wang et al. |
| 2007/0028667 A1 | 2/2007 | Kim et al. |
| 2007/0045114 A1 | 3/2007 | Wang et al. |
| 2007/0105341 A1 | 5/2007 | Sosnowchik et al. |
| 2007/0212263 A1 | 9/2007 | Shin et al. |
| 2008/0093226 A1 | 4/2008 | Briman et al. |
| 2008/0148815 A1 | 6/2008 | Lucas et al. |
| 2009/0218235 A1 | 9/2009 | McDonald et al. |
| 2009/0235862 A1 | 9/2009 | Cha et al. |
| 2009/0249859 A1 | 10/2009 | Takahashi |
| 2010/0213603 A1 | 8/2010 | Smeys et al. |
| 2011/0128828 A1 | 6/2011 | Naniwa et al. |
| 2011/0149465 A1 | 6/2011 | Hashimoto et al. |
| 2012/0041246 A1 | 2/2012 | Scher et al. |
| 2012/0192623 A1 | 8/2012 | Adami et al. |
| 2012/0297860 A1 | 11/2012 | Izawa et al. |
| 2012/0301360 A1 | 11/2012 | Meinhold et al. |
| 2014/0036953 A1 | 2/2014 | Kimura et al. |
| 2014/0208828 A1 | 7/2014 | Von Waldkirch |
| 2014/0212979 A1 | 7/2014 | Burgi et al. |
| 2015/0316523 A1 | 11/2015 | Patolsky et al. |
| 2017/0276627 A1 | 9/2017 | Dobrokhotov et al. |
| 2018/0024089 A1 | 1/2018 | Mickelson et al. |
| 2018/0031532 A1 | 2/2018 | Lee et al. |
| 2018/0313800 A1 | 11/2018 | Rogers et al. |
| 2020/0393432 A1 | 12/2020 | Swanson et al. |
| 2022/0146481 A1 | 5/2022 | Ricci et al. |

FOREIGN PATENT DOCUMENTS

| | | |
|---|---|---|
| JP | 2001250909 A | 9/2001 |
| JP | 2017102131 A | 6/2017 |
| RU | 2709051 C1 | 12/2019 |
| WO | WO-9947905 A2 | 9/1999 |
| WO | WO-2019083939 A1 | 5/2019 |

OTHER PUBLICATIONS

Banerjee et al., "The Detection of Improvised Nonmilitary Peroxide Based Explosives Using a Titania Nanotube Array Sensor," Nanotechnology, 20—pp. 1-6 (Jan. 2009).

Buttigieg et al. "Characterization of the Explosive Triacetone Triperoxide and Detection by Ion Mobility Spectrometry," Forensic Science International 135:53-59 (Apr. 2003).

Campos et al. "An Electronic Tongue Designed to Detect Ammonium Nitrate in Aqueous Solutions," Sensors, 13:14064-14078 (Oct. 2013).

Cho et al., "Colorimetric Sensors for Toxic and Hazardous Gas Detection: A Review," Electronic Materials Letters, 17:1-17 (Published Online Nov. 2020).

Choodum et al., "On-site semi-quantitative analysis for ammonium nitrate detection using digital image colourimetry," Science and Justice, 55:437-445 (May 2015).

Chu, et al., "Detection of Peroxides Using Pd/SnO2(subscript) Nanocomposite Catalysts," Sensors and Actuators B: Chemical, 197:376-384 (Jul. 2014).

Das et al. "Enhanced Response of Co-Planar MEMS Microheater-Based Methane Gas Sensor," IEEE Sensors Journal, 20(23):14132-14140 (Dec. 2020).

De Perre et al. "Rapid and specific detection of urea nitrate and ammonium nitrate by electrospray ionization time-of-flight mass spectrometry using infusion with crown ethers," Rapid Commun. Mass Spectrom., 26:154-162 (2012).

Dong et al., "Simulation of the columnar-to-equiaxed transition in directionally solidified Al-Cu alloys," Acta Materialia, 53:659-668 (2005).

Ewing et al., "A critical review of ion mobility spectrometry for the detection of explosives and explosive related compounds," Talanta, 54:515-529 (2001).

Ewing et al., "Direct Real-Time Detection of RDX Vapors Under Ambient Conditions," Anal. Chem., 85:389-397 (2013).

Ewing et al., "The vapor pressures of explosives," Trends in Analytical Chemistry, 42:35-48 (2013).

Germain et al., "Turn-on Fluorescence Detection of H2O2 and TAPT," Inorganic Chemistry, 47(21):9748-9750 (2008).

Gopalakrishnan et al., "Direct Detection of RDX Vapor Using a Conjugated Polymer Network," J. Am. Chem. Soc., 135:8357-8362 (May 2013).

Hampton, M., "Wanted: A Bomb Detector as Sensitive as a Dog's Nose," IEEE Spectrum, Oct. 11, 2019, https://spectrum.ieee.org/tech-talk/semiconductors/devices/using-a-twopronged-approach-to-detect-explosive-substances-from-bombs.

Hsueh et al. "A transparent ZnO nanowire MEMS gas sensor prepared by an ITO micro-heater," Sensors & Actuators B:Chemical, 304:127319 (2020).

Hwang et al., "Development of Micro-Heaters with Optimized Temperature Compensation Design for Gas Sensors," Sensors, 11:2580-2591 (Mar. 2011).

Hwang et al., "Gas sensing properties of SnO2 nanowires on micro-heater," Sensors & Actuators B: Chemical, 154:295-300 (2011).

Jung et al., "A low-power embedded poly-Si micro-heater for gas sensor platform based on a FET transducer and its application for NO2 sensing," Sensors & Actuators: B Chemical, 334:129642 (Feb. 2021).

Lee et al., "Highly Sensitive and Multifunctional Tactile Sensor Using Free-standing ZnO/PVDF Thin Film with Graphene Electrodes for Pressure and Temperature Monitoring," Scientific Reports, 5 (7887):1-8 (Jan. 2015).

Lin et al., "A Colorimetric Sensor Array for Detection of Triacetone Triperoxide Vapor," J. Am. Chem. Soc., 132 (44):15519-15521 (Oct. 2010).

Ma et al., "Ultrasensitive, Specific, and Rapid Fluorescence Turn-On Nitrite Sensor Enabled by Precisely Modulated Fluorophore Binding," Adv. Sci., 7:2002991 (1-11), (Nov. 2020).

Malashikhin et al., "Fluorescent Signaling Based on Sulfoxide Profluorophores: Application to the Visual Detection of the Explosive TATP," J. Am. Chem. Soc., 130:12846-12847 (Apr. 2008).

Mallin, Daniel, "Increasing the Selectivity and Sensitivity of Gas Sensors for the Detection of Explosives," Master Thesis, University of Rhode Island (2014).

Moalaghi et al., "Tin oxide gas sensor on tin oxide microheater for high-temperature methane sensing," Material Letters, 263:127196 , 4 pages (Mar. 2020).

Mullen et al., " Laser photoionization of triacetone triperoxide (TATP) by femtosecond and nanosecond laser pulses," International Journal of Mass Spectrometry, 252:69-72 (Feb. 2006).

Mullen et al., "Detection of Explosives and Explosives-Related Compounds by Single Photon Laser Ionization Time-of-Flight mass Spectrometry," Anal. Chem., 78(11):3807-3814 (Jun. 2006).

(56) References Cited

OTHER PUBLICATIONS

Rasanen et al., "Determination of gas phase triacetone triperoxide with aspiration ion mobility spectrometry and gas chromatography-mass spectrometry," Analytica Chimica ACTA, 623:59-65 (Jun. 2008).
Ricci et al., "Continuous Monitoring of TATP Using Ultrasensitive, Low-Power Sensors," IEEE Sensors Journal, 20(23):14058-14064 (Dec. 2020).
Ricci et al., "Sensors for the detection of ammonia as a potential biomarker for health screening," Scientific Reports, 11:7185 pp. 1-7 (Mar. 2021).
Ricci et al., "Free-standing, thin-film sensors for the trace detection of explosives," Scientific Reports, 11:6623, 10 pages (Mar. 2021).
Ricci et al., "Orthogonal Sensors for the Trace Detection of Explosives," IEEE Sensors Letters, 3(10):1-4 (Oct. 2019).
Rossi et al., "Trace Detection of Explosives Using Metal Oxide Catalysts," IEEE Sensors Journal, 19(13):4773-4780 (Jul. 2019).
Schulte-Ladbeck et al., "Determination of Peroxide-Based Explosives using Liquid Chromatography with On-Line Infrared Detection," Anal. Chem., 78(23):8150-8155 (Dec. 2006).
Schulte-Ladbeck et al., "Trace Analysis of Peroxide-Based Explosives," Anal. Chem., 75(4):731-735 (Feb. 2003).
Sigman et al., "Analysis of triacetone triperoxide by gas chromatography/mass spectrometry and gas chromatography/tandem mass spectrometry by electron and chemical ionization," Rapid Commun. Mass Spectrom., 20:2851-2857 (Jul. 2006).
Stambouli et al., "Headspace-GC/MS detection of TATP traces in post-explosion debris," Forensic Science International, 146S:S191-S194 (Dec. 2004).
Subramanian et al., "Cu—Pd (Copper-Palladium)," Journal of Phase Equilibria., 12(2):231-243 (1991).
Suematsu et al., "Pulse-Driven Semiconductor Gas Sensors Toward ppt Level Toluene Detection," Anal. Chem., 90:11219-11223 (Aug. 2018).
Sysoev, et al., Percolating SnO2 nanowire network as a stable gas sensor: Direct comparison of long-term performance versus SnO2 nanoparticle films, Sensors and Actuators B, 139(2):699-703 (Jun. 2009).
To et al., "Recent Developments in the Field of Explosive Trace Detection," ACS Nano., 14:10804-10833 (Aug. 2020).
Tong et al., "A fast response and recovery H2S gas sensor based on free-standing TiO2 nanotube array films prepared by one step anodization method," Ceramics International, 43:14200-14209 (Jul. 2017).
Wang et al., "A Colorimetric Artificial Olfactory System for Airborne Improvised Explosive Identification," Adv. Mater., 32(14):1907043, 11 pages (Apr. 2020).
Wang et al., "A MEMS-based Air Flow Sensor with a Free-standing Micro-cantilever Structure," Sensors, 7(10):2389-2401 (Oct. 2007).
Wu et al., "Improved Selectivity and Sensitivity of Gas Sensing Using a 3D Reduced Graphene Oxide Hydrogel with an Integrated Microheater," ACS App. Mater. Interfaces, 7(49):27502-27510 (Dec. 2015).
Xu et al., "Surface Plasmon Resonances of Free-Standing Gold Nanowires Fabricated by Nanoskiving," Angew. Chem. Int. Ed., 45(22):3631-3635 (May 2006).
U.S. Appl. No. 17/356,392, filed Jun. 23, 2021.
U.S. Appl. No. 17/453,620, filed Nov. 4, 2021.
U.S. Appl. No. 17/659,980, filed Apr. 20, 2022.
International Search Report & Written Opinion dated Aug. 30, 2022 in Int'l PCT Patent Appl. Serial No. PCT/US2021/072250.
International Search Report & Written Opinion dated Oct. 12, 2022 in Int'l PCT Patent Appl. Serial No. PCT/US2022/073061.
Sevedjalah, et al., thick in the air, Electronics Letter, 51(11):799 (May 28, 2015).

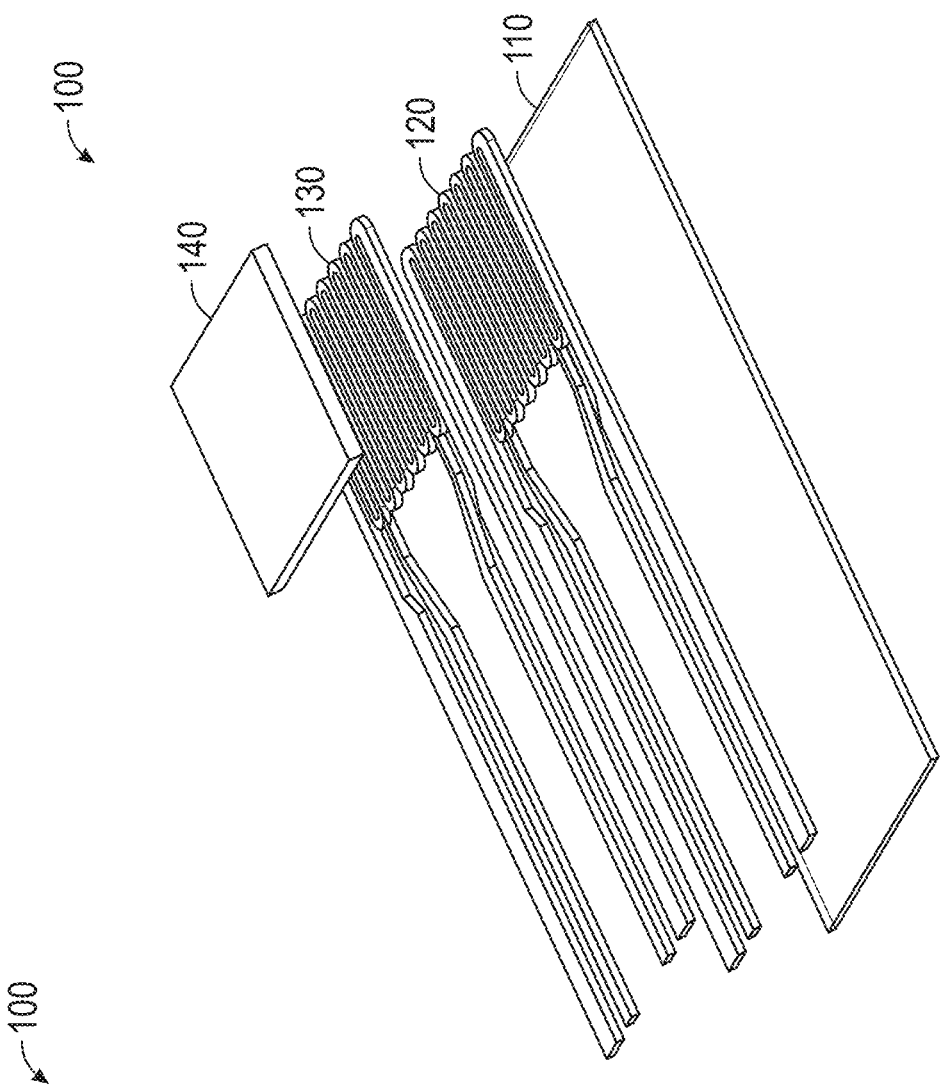
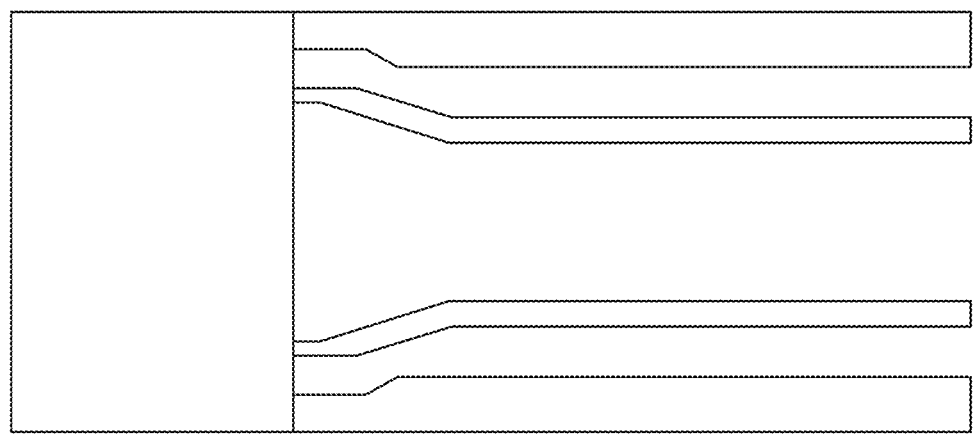

1700 ⤴

| | Al₂CuO₄ | Fe₂O₃ | ITO | CuO | SnO | WO |
|---|---|---|---|---|---|---|
| Optimal Operating Temperature (°C) | 250 | 175 | 175 | 250 | 175 | 250 |
| CBD (13ppt) | NR | + | + | - | + | + |
| Fentanyl (11ppt) | NR | NR | + | NR | + | NR |
| THC (0.15ppt) | - | - | + | - | + | + |

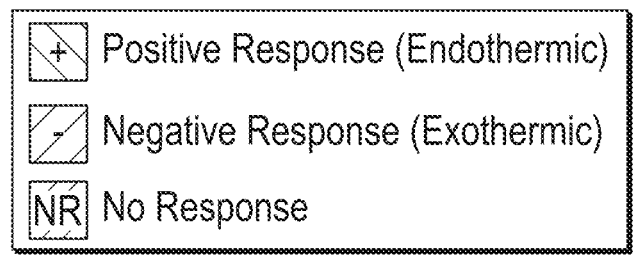

Legend: + Positive Response (Endothermic); − Negative Response (Exothermic); NR No Response

| | Al₂CuO₄ | Fe₂O₃ | ITO | MnO | SnO | WO |
|---|---|---|---|---|---|---|
| Optimal Operating Temperature (°C) | 250 | 175 | 175 | 250 | 175 | 250 |
| Glucose (15ppt) | NR | NR | + | - | + | - |
| Fructose (15ppt) | NR | - | + | - | + | NR |
| Ammonia (7ppm) | NR | - | + | - | - | + |
| H₂O₂ (7ppm) | + | - | - | + | - | + |

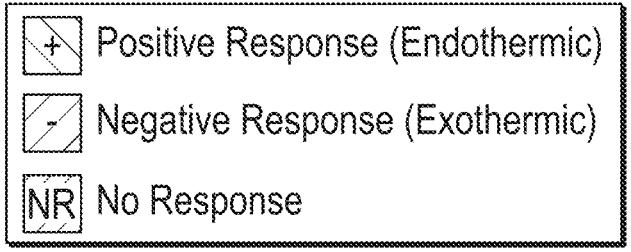

Legend: + Positive Response (Endothermic); − Negative Response (Exothermic); NR No Response

| | Al$_2$CuO$_4$ | Fe$_2$O$_3$ | ITO | MnO | SnO | WO |
|---|---|---|---|---|---|---|
| Optimal Operating Temperature (°C) | 250 | 175 | 175 | 250 | 175 | 250 |
| Natural Gas (7ppm) | + | − | + | + | + | + |
| Acetone (10ppm) | − | − | + | − | + | − |
| Methanol (15ppm) | − | − | + | − | + | + |

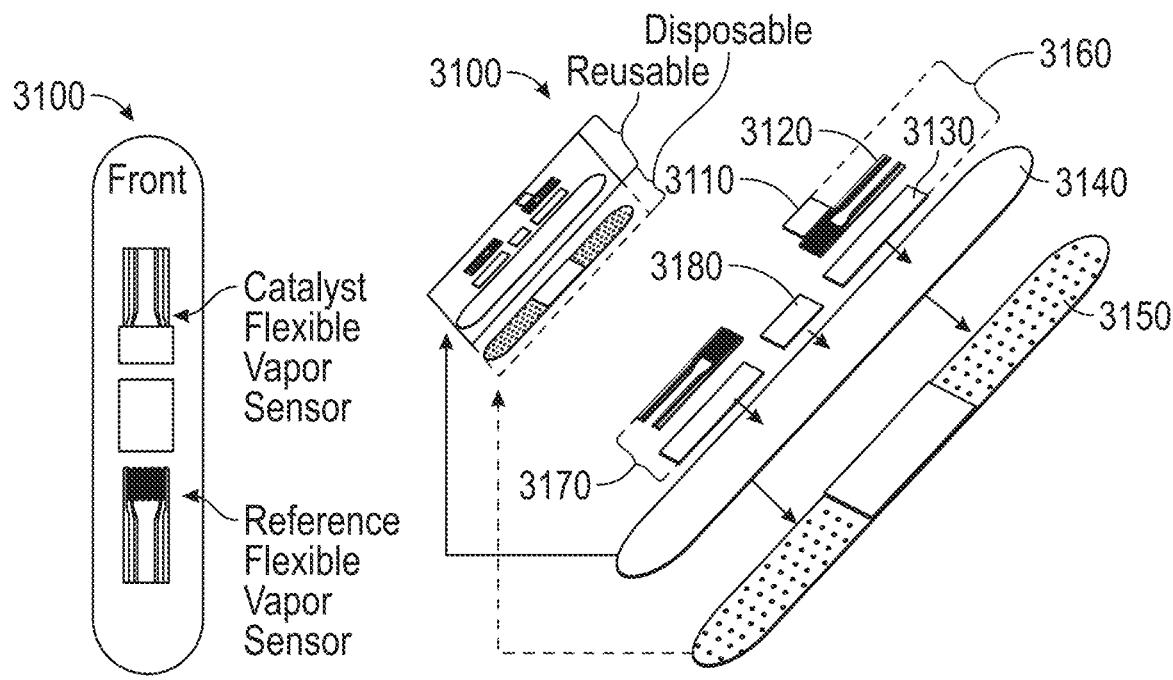
FIG. 31A
FIG. 31B
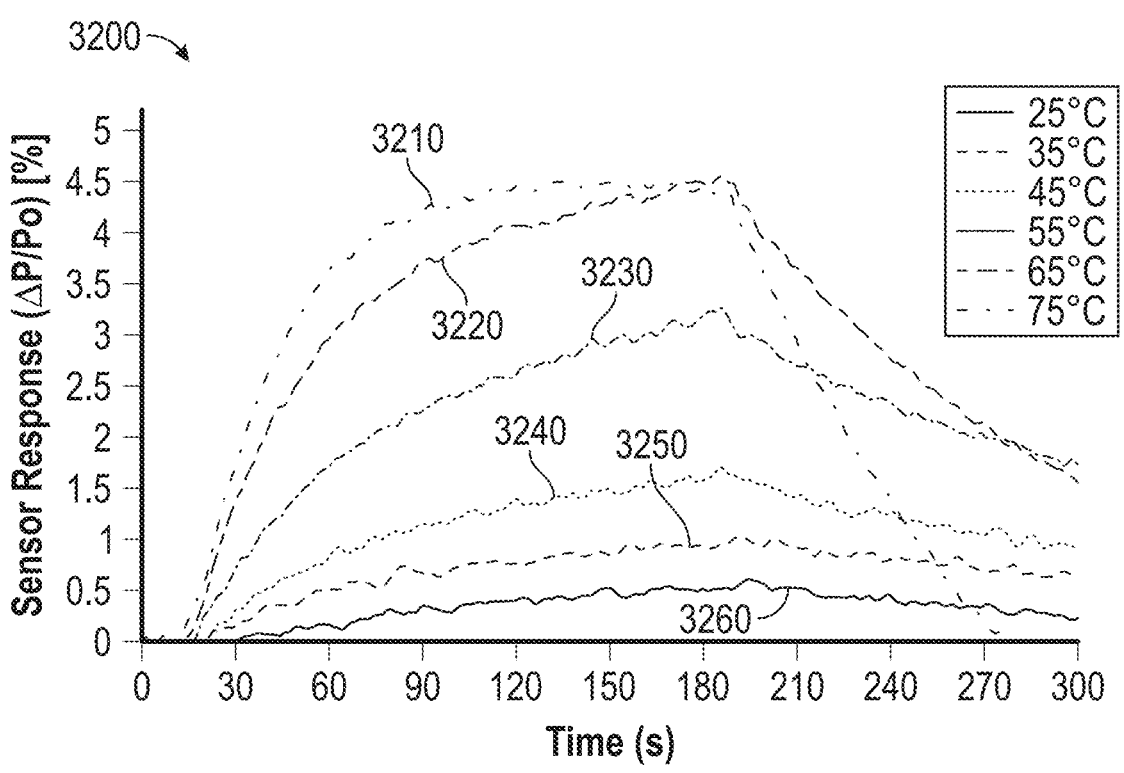
FIG. 32

ULTRASENSITIVE, ULTRATHIN VAPOR SENSORS AND ARRAYS

CROSS-REFERENCE TO RELATED APPLICATIONS

This application is a continuation-in-part application from U.S. patent application Ser. No. 17/356,392, filed Jun. 23, 2021, the entire contents of which are incorporated herein by reference.

TECHNICAL FIELD

The present disclosure describes an ultrasensitive, ultrathin thermodynamic sensing platform for the detection of chemical compounds in the vapor phase at trace levels. This thermodynamic sensor platform may be referred to herein as an "ultrathin vapor sensor." The detection system described within has been used to detect chemical compounds, including explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

BACKGROUND

Sensors utilizing microheaters have been shown to be effective in detecting explosives such as triacetone triperoxide (TATP) in the vapor phase at trace levels. Such sensors include those described in U.S. Pat. No. 9,759,699 to Gregory et al. and Chu et al., "Detection of Peroxides using $Pd/SnO_2$ Catalysts" published on 5 Jul. 2014 in Sensors and Actuators B: Chemical, the entire contents of each of which are incorporated herein by reference. While those sensors are extremely effective, it is desirable to provide sensors having increased sensitivity.

Those existing chemical sensors comprise relatively thick (measured in hundreds of micrometers) alumina substrates, relatively thick nickel films for the microheaters, and a thick passivation layer between the heater and the catalyst. Additionally, a temperature of approximately 500° C. is required to operate these sensors, and therefore a significant amount of power is required for the heaters. The relatively large thermal mass of the components of these sensors further adds to the required power to operate. Additionally, these sensors contained a substrate that was isotropic, which transferred heat laterally. This large thermal mass in combination with the lateral heat transfer was found to affect the accuracy of the heat measurements of the catalyst.

Other known sensors attempt to reduce the thermal mass. For example, sensors were manufactured having free-standing 25-micrometer nickel wire microheaters and no substrate. Such sensors demonstrated improved sensor response time and sensitivity. Nevertheless, these sensors had drastically reduced catalytic surface area, which limited their catalytic activity.

In view of the foregoing drawbacks of previously known systems, there exists a need for chemical sensors that operate at less than 500° C.

It further would be desirable to have chemical sensors that have a reduced thermal mass.

It further would be desirable to have chemical sensors that require less power to operate than some known systems.

It further would be desirable to have chemical sensors that are capable of detection of substances in extremely low concentrations.

It further would be desirable to have chemical sensors that are capable of detection of substances at near room temperature.

It further would be desirable to have chemical sensors that are flexible and wearable.

SUMMARY

Provided herein are ultrathin, low power vapor sensors with extremely high sensitivity. Embodiments of the sensor operate at temperatures much lower than 500° C., have a reduced thermal mass, and use less power than known sensors. Moreover, embodiments of a ultrathin, low power vapor sensor in accordance with the present invention are highly sensitive and are capable of detecting chemicals at concentration levels as low as in parts per trillion (ppt).

In some preferred embodiments, the sensors comprise a Pd-based microheater deposited onto ultrathin (<40 μm thick) yttria-stabilized-zirconia substrate, which results in increased sensor sensitivity and selectivity over known devices. In some preferred embodiments, the sensors comprise an aerogel substrate, which provides increased flexibility that may be beneficial for applications such as wearables. Embodiments of an ultrathin, low power vapor sensor display highly anisotropic thermal characteristics, which result in highly localized heating with corresponding improvements to the power efficiency. Embodiments of an ultrathin, low power vapor sensor have displayed the ability to detect one or more chemical compounds in the vapor phase at trace levels with relatively minimal power requirements.

In accordance with some aspects, a detection device is provided that includes at least one multi-layer sensor. In some embodiments, the sensor(s) has four layers. For example, the sensor may include a first layer having a substrate, a second layer in contact with the first layer, a third layer in contact with the second layer, and a fourth layer in contact with the third layer. The second layer may be an adhesion layer. The third layer may be a metallic microheater configured to receive power at a first power level to reach a setpoint temperature. The fourth layer may include a catalyst configured to undergo a chemical reaction when exposed to an analyte. The chemical reaction may be endothermic or exothermic. The metallic microheater may receive power at a second power level to maintain the setpoint temperature after the catalyst begins the chemical reaction. A heat effect indicative of information on the analyte may be determined by comparing the second power level to the first power level.

In some embodiments, the substrate is yttria-stabilized-zirconia. In some embodiments, the substrate is aerogel. The adhesion layer may be copper. The metallic microheater may be palladium. The catalyst may be a metal oxide catalyst. The substrate may have a thickness of less than 40 micrometers.

The detection device may detect the analyte in a vapor phase based on the heat effect. The detection device may detect the analyte at concentration levels as low as in parts per trillion (ppt).

The detection device may include a controller configured to cause the power to be provided at the first power level to reach the setpoint temperature, to cause the power to be provided at the second power level to maintain the setpoint temperature after the catalyst begins the chemical reaction, and determine an existence, identity, and/or concentration of the analyte based on comparing the second power level to the first power level. As will be readily understood, the detection device may determine the existence, identity, and/or concentration of one or more additional analytes as well.

The detection device may include a reference sensor that is not coated with a catalyst. The detection device may include a second sensor having a second microheater in thermal communication with a second catalyst different from the first catalyst. The detection device may include third, fourth, and fifth sensors comprising third, fourth, and fifth catalysts, respectively.

In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO).

In accordance with some aspects, a detection device is provided with an array of sensors that are electrically coupled to a controller. Each sensor in the array may have its own distinct catalyst such that reactions between an analyte(s) and the distinct catalysts (to the extent a reaction occurs) indicate information on the existence, identity, and/or concentration of the analyte(s). For example, the reactions may be thermal and the controller may monitor the variations in power applied to each sensor to determine the existence, identity, and/or concentration of the analyte(s). Each of the sensors in the array may be formed from the multi-layer configuration described above with its own distinct catalyst. A reference sensor may be included in the array that is formed in the multi-layer manner, but without a catalyst.

In some embodiments, a first sensor has a first microheater and a first catalyst in thermal communication with the first microheater and a second sensor has a second microheater layer and a second catalyst layer in thermal communication with the second microheater layer. The controller in electrical communication with the first sensor and the second sensor. The controller may cause power to be provided to the first and second sensors to heat the first sensor to a first setpoint temperature and to heat the second sensor to a second setpoint temperature, vary power applied to the first sensor and/or the second sensor to account for a thermal response caused by reactions between an analyte and the first catalyst layer and/or the second catalyst layer to maintain the first setpoint temperature and the second setpoint temperature, and determine an existence, identity, and/or concentration of the analyte based on the varied the power. The first setpoint temperature may be the same temperature as the second setpoint temperature.

In some embodiments, the detection device includes a reference sensor having a reference microheater and without a catalyst, the reference sensor in electrical communication with the controller. The detection device may include a third sensor comprising a third microheater and a third catalyst in thermal communication with the third microheater, a fourth sensor comprising a fourth microheater and a fourth catalyst in thermal communication with the fourth microheater, and a fifth sensor comprising a fifth microheater and a fifth catalyst in thermal communication with the fifth microheater. In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO). As will be readily understood, the detection device may include more than six sensors and the additional sensors preferably have their own distinct catalyst.

In some embodiments, the first catalyst, the second catalyst, the third catalyst, the fourth catalyst, and the fifth catalyst each comprise aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). The setpoint temperature may be between 50° C. and 500° C.

In accordance with some aspects, a method of detecting an analyte is provided. The method may include providing a sensor array comprising a first sensor and a second sensor, the first sensor comprising a first microheater layer and a first catalyst layer in thermal communication with the first microheater layer, the second sensor comprising a second microheater layer and a second catalyst layer in thermal communication with the second microheater layer; delivering power to the first and second sensors to heat the first sensor to a first setpoint temperature and to heat the second sensor to a second setpoint temperature; exposing the first and second sensors to an analyte such that the first catalyst layer and/or the second catalyst layer react with the analyte to generate a thermal response; varying power applied to the first sensor and/or the second sensor to account for the thermal response to maintain the first setpoint temperature and the second setpoint temperature; and/or determining an existence, identity, and/or concentration of the analyte based on varying the power.

Determining the existence, identity, and/or concentration of the analyte based on varying the power may include comparing the thermal response to a database of known thermal responses. The sensor array may include a reference sensor and determining the existence, identity, and/or concentration of the analyte may include analyzing information on power supplied to the reference sensor. In some embodiments, the first catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). In some embodiments, the second catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

The detection device described herein may be used to detect a variety of analytes including but not limited to explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

BRIEF DESCRIPTION OF THE DRAWINGS

FIG. 1A shows a top view an embodiment of a detection device.

FIG. 1B shows an exploded view of an embodiment of a detection device.

FIG. 17 shows a summary table consisting of the thermodynamic sign indicative of the measured redox reactions, for six catalysts making up an ultrathin vapor sensor array.

FIG. 18 shows a summary table consisting of the thermodynamic sign indicative of the measured redox reactions, for six catalysts making up an ultrathin vapor sensor array.

FIG. 31A shows a top view an embodiment of a detection device for skin sensing applications.

FIG. 31B shows an exploded view of an embodiment of a detection device for skin sensing applications.

FIG. 32 shows an illustrative graphical representation of a comparison between responses of a flexible vapor sensor employing an ITO catalyst to 7 ppm $H_2O_2$ at a variety of operating temperatures near room temperature.

DETAILED DESCRIPTION OF THE PREFERRED EMBODIMENTS

Figure 1C:
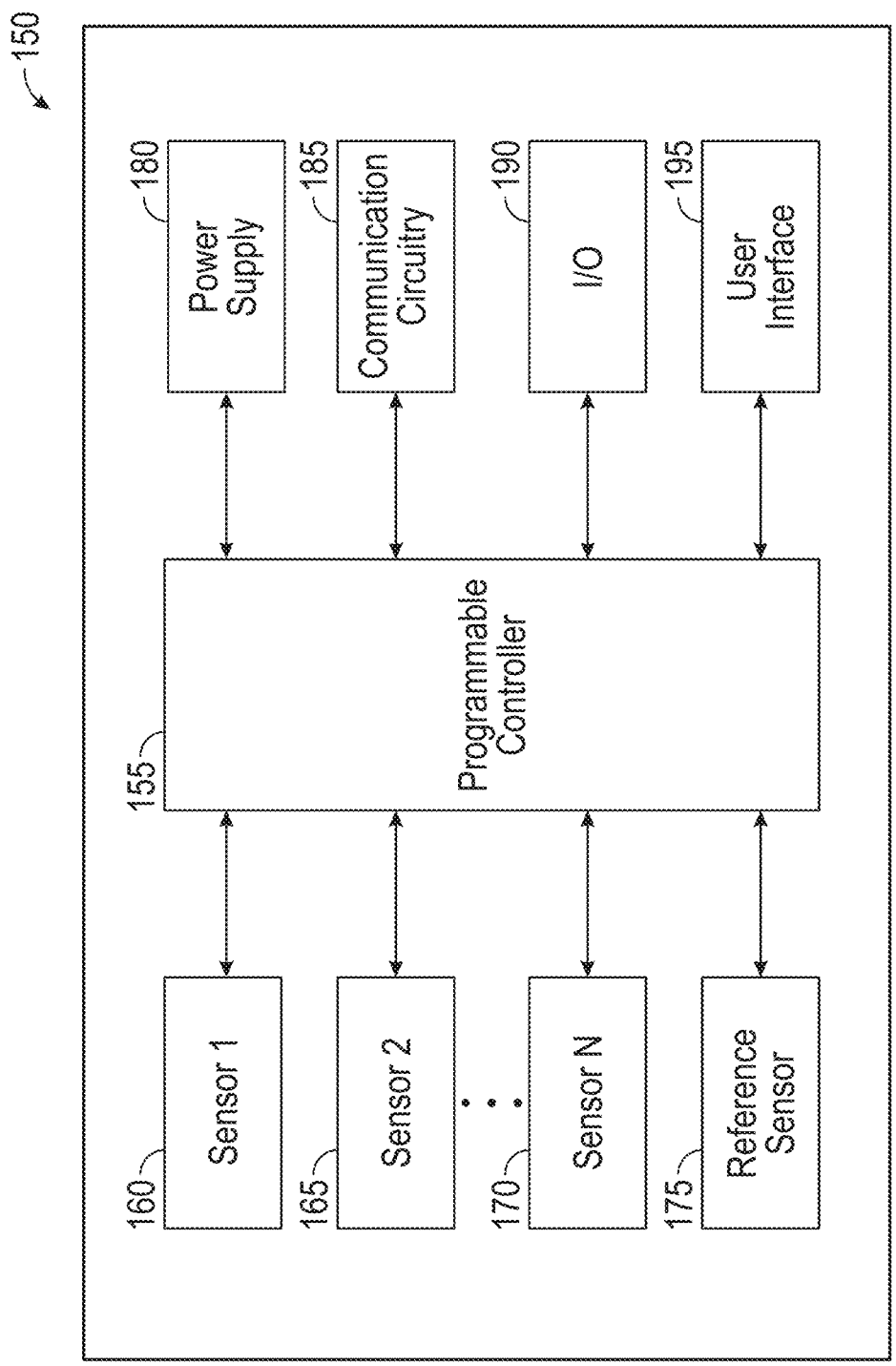
FIG. 1C shows a schematic diagram of an exemplary detection device.

Described herein are ultrathin vapor sensors utilizing thin film microheaters deposited onto ultrathin substrates, such as yttria-stabilized zirconia (YSZ) ceramic and/or aerogel substrates. Embodiments of the present invention are capable of detecting trace levels of compounds in the gas phase. Embodiments of the ultrathin vapor sensors comprise at least two microheaters, one or more catalyst coated "active" microheaters and an uncoated "reference" microheater. The microheaters are thermally scanned over a selected temperature range and electrically powered, and preferably are configured to maintain a constant temperature. Upon reaching a set temperature, the power difference between the reference (uncoated) microheater and a catalyst coated microheater may be measured. This electrical power difference is the heat effect associated with oxidation/reduction reactions that occur on the surface of the catalyst after decomposition of a target molecule has occurred.

Measurement of the power difference between a sensor and the reference may be obtained utilizing a controller integrating Wheatstone bridge circuitry, or more preferably a half-Wheatstone bridge or an Anderson loop for increased efficiency. It will be appreciated that changes in the electrical power of the reference microheater and the catalyst coated microheater may be used to calculate the power difference and thus, the response of the sensor platform.

In operation of embodiments, the reference (uncoated) microheater and the catalyst coated microheaters are electrically powered to a predetermined setpoint temperature. Upon introduction of the analyte, the vapor sensor qualitatively or quantitatively measures the heat effect associated with interactions between the catalyst and the analyte. In general, oxidation reactions release heat, resulting in less electrical power required to maintain the same temperature and are therefore associated with negative responses. Conversely, reduction reactions absorb heat requiring more electrical power to maintain the same temperature and are therefore associated with positive responses. These heat effects are the result of oxidation/reduction reactions on the catalyst surface and the catalytic decomposition of the target molecule. The reference sensor is used to monitor sensible heat effects and other hydrodynamic effects, thus, mitigating false positives/negatives. As a result, the heat effect may be quantified, as well as qualified as endothermic, exothermic, or neither. Different catalysts used in different sensors in the detection system may experience a different heat effect when exposed to the same analyte. By comparing the quantitative or qualitative results from a plurality of sensors of a system to known results, the existence and concentration of an analyte may be determined.

The detection system described herein may be used to detect chemical compounds, including explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

Experiments employing aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO) catalysts were performed. As a result of experiments using sensors comprising ultrathin YSZ ceramic substrates, the sensing mechanism was confirmed for a number of these analytes.

Reducing the thermal mass of the sensing platform further by utilizing ultrathin YSZ as the substrate for the thin film microheaters yielded some unexpected results. For example, the enhanced catalytic surface area (relative to freestanding wire sensors) combined with a reduced substrate thickness resulted in the ultrathin vapor sensor having a lower thermal mass without sacrificing catalytic surface area. In preferred embodiments of the present invention, the substrates are preferably thin YSZ substrates, such as 3 mol % YSZ having a thickness of between approximately 5 micrometers and 100 micrometers, more preferably between approximately 10 micrometers and 40 micrometers, and most preferably approximately 20 micrometers. The ultrathin YSZ substrate is preferably thermally anisotropic, so that the heat is highly localized in the "z" direction (perpendicular to the surface of the substrate). This result was more desirable than results seen with the alumina substrates used in known solid-state sensors, in which the heat is laterally spread. The thermal properties of embodiments of preferred embodiments are highly anisotropic in that the in-plane thermal conductivity of the YSZ (2.7 W/mK) is significantly lower than that of the alumina (30 W/mK). This difference causes the more of heat in ultrathin vapor sensors to remain in the area of catalyst, as compared to known systems employing alumina in which the heat without dissipates laterally to other areas of the sensor platform. As a result of this difference in heat transfer, there is a significant decrease in the temperature required for chemical detection, as well as a reduction in the power required to operate the sensor. For example, detection of compounds in the parts-per-million (ppm) and parts-per-billion (ppb) range is now possible at temperatures between 75° C. and 275° C. using embodiments of the ultrathin vapor sensors. Because more of the thermal energy is focused in the vicinity of the microheater and does not spread to other areas of the substrate as compared to previously-known systems, the resolution of the measurement of the inventive systems is also improved.

FIG. 1A and FIG. 1B show a top view of detection device 100, which may be an ultrathin vapor sensor, and an exploded view of detection device 100, respectively. As illustrated in FIG. 1B, detection device 100 may include multiple layers such as substrate layer 110, adhesion layer 120, microheater layer 130, and catalyst layer 140.

In preferred embodiments, substrate 110 is ultrathin YSZ substrate, which comprises a nominal thickness (e.g., 20 micrometers). Notably, layers of ultrathin vapor sensor 100 may have different thicknesses, and the films may be optimized for thickness to maximize surface area of the metal oxide catalyst while still maintaining the low mass characteristics of the microheater. Substrate 110 may be an aerogel substrate, as described in detail below.

Adhesion layer 120 may be in contact with substrate layer 110 and microheater layer 130, as illustrated. Adhesion layer 120 may be formed of a metal such as copper. Adhesion layer 120 may have the same shape as microheater layer 130 as illustrated.

Microheater layer 130 may be formed of metal. Microheater layer 130 is designed maintain a setpoint temperature via the addition or reduction of heat upon exposure to an endothermic or exothermic chemical reaction, respectively, at catalyst layer 140. In some embodiments, microheater 130 is formed using photolithography to pattern a 1-micrometer thick palladium film microheater, which has considerably lower thermal mass than free-standing 25-micrometer diameter nickel wires used in previously-known sensors that have a much higher surface area. Palladium is a preferred choice for the metallization due to its catalytic amplification effect, which has been shown to improve sensitivity and response time.

Catalyst layer 140 is coated with a catalyst selected for detection of a predetermined analyte. The catalyst may be selected to chemically react with the analyte selected for detection.

FIG. 1C illustrates a generalized schematic diagram of the internal functional components of an exemplary detection device. Detection device 150 includes a plurality of sensors in communication with programmable controller 155. The plurality of sensors includes first sensor 160, second sensor 165, and so forth up to and including Nth sensor 170. Each of sensors 160, 165, 170 may be constructed in the manner described for the sensor in FIGS. 1A and 1B, although in some embodiments, each sensor has a different catalyst. Sensors also may include reference sensor 175, which may be constructed in the manner described for the sensor in FIGS. 1A and 1B, although the reference sensor preferably does not include a catalyst. Programmable controller 155 is in electronic communication with each of the plurality of sensors. Specifically, programmable controller 155 may provide a known amount of power to each of the plurality of sensors, though it will be appreciated that in some uses not all of the sensors will be necessary and in such cases programmable controller 155 may selectively provide power to the subset of the sensors that are necessary. Programmable controller 155 is configured to determine the amount of power provided to each of the sensors and to compare the power provided to any individual sensor (e.g., Nth sensor 170) to the power provided to reference sensor 175. Programmable controller 155 may integrate Wheatstone bride circuitry for each sensor, or more preferably a half-Wheatstone bridge or an Anderson loop for increased efficiency.

Detection device 150 further includes power supply 180, communication circuitry 185, input/output 190 and user interface 195, each of which are coupled to controller 155.

User interface 195 may be used to receive inputs from, and provide outputs to, a user. For example, user interface 195 may provide information to the user on the existence, identity, and/or concentration of an analyte detected by detection device 150. User interface 195 may include a power switch that completes a circuit between power supply 180 and controller 155 to selectively activate an operational mode of device 155. User interface 195 may include a setpoint temperature controller, wherein the user may select one or more operating temperatures for the plurality of sensors. User interface 195 may further include a volume control to selectively increase or decrease an audio output.

User interface 195 may include a touchscreen, switches, dials, lights, an LED matrix, other LED indicators, or other input/output devices for receiving inputs from, and providing outputs to, a user. In other embodiments, user interface 404 is not present on detection device 150, but is instead provided on a remote computing device communicatively connected to detection device 150 via the communication circuitry 185. User interface also may be a combination of elements on the detection device and a remote computing device.

Input and output circuitry (I/O) 190 may include ports for data communication such as wired communication with a computer and/or ports for receiving removable memory, e.g., SD card, upon which program instructions or data related to known reactions may be stored and/or for transmitting power to detection device 150. In one embodiment, I/O 190 comprises ports, and corresponding circuitry, for accepting cables such that controller 155 is electrically coupled to an externally located computer system.

Power supply 180 may supply alternating current or direct current. In direct current embodiments, power supply may include a suitable battery such as a replaceable battery or rechargeable battery and apparatus may include circuitry for charging the rechargeable battery, and a detachable power cord. Power supply 180 may be charged by a charger via an inductive coil within the charger and inductive coil. Alternatively, power supply 180 may be a port to allow device 155 to be plugged into a conventional wall socket, e.g., via a cord with an AC to DC power converter, for powering components within the device. Power supply 180 may be designed to supply power to the components of detection device 150. For example, power supply 180 may, responsive to instructions by controller 155, supply power to each of the sensors to maintain a setpoint temperature(s) and to vary the power supplied to each of the sensors to maintain the setpoint temperature(s) as the respective catalysts undergo thermal reactions with an analyte (if present).

Controller 155 includes electrical components and permits electrical coupling between controller 155 and sensors (e.g., first sensor 160, second sensor 165, N additional sensors 170, reference sensor 175) and other components, when included, such as communication circuitry 185, input/output 190, and user interface 195. Controller includes memory, which may be RAM, ROM, Flash, or other known memory, or some combination thereof. Controller preferably includes storage in which data may be selectively saved. For example, programmable instructions may be stored to execute algorithms for detecting the existence, identity, and/or concentration of an analyte based on the amount of power the controller causes to be supplied to each of the sensors in the array. The instructions may utilize information stored (e.g., in lookup tables) to determine information on the analyte. One or more electrical components and/or circuits may perform some of or all the roles of the various components described herein. Although described separately, it is to be appreciated that electrical components need not be separate structural elements. For example, controller 155 and communication circuitry 185 may be embodied in a single chip. In addition, while controller 155 is described as having memory, a memory chip(s) may be separately provided.

Controller 155 may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A controller may also be implemented as a combination of computing devices, e.g., a combination of a DSP and a microprocessor, a plurality of microprocessors, one or more microprocessors in conjunction with a DSP core, or any other such configuration.

Controller 155 may contain memory and/or be coupled, via one or more buses, to read information from, or write information to, memory. The memory may include processor cache, including a multi-level hierarchical cache in which different levels have different capacities and access speeds. The memory may also include random access memory (RAM), other volatile storage devices, or non-volatile storage devices. The storage devices can include, for example, hard drives, optical discs, flash memory, and Zip drives.

Controller 155, in conjunction with firmware/software stored in the memory may execute an operating system, such as, for example, Windows, Mac OS, Unix or Solaris 5.10. Controller 155 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuitry 185 is configured to transmit information, such as signals indicative of the presence, absence, and/or quantity of one or more target analytes, locally and/or to a remote location such as a server. Communication circuitry 185 is configured for wired and/or wireless communication over a network such as the Internet, a telephone network, a Bluetooth network, and/or a WiFi network using techniques known in the art. Communication circuitry 185 may be a communication chip known in the art such as a Bluetooth chip and/or a WiFi chip. Communication circuitry 185 may include a receiver and a transmitter, or a transceiver, for wirelessly receiving data from, and transmitting data to a remote computing device. In some such embodiments, the remote computing device may be a mobile computing device that provides the system with a user interface; additionally or alternatively, the remote computing device is a server. In embodiments configured for wireless communication with other devices, communication circuitry 185 may prepare data generated by controller 155 for transmission over a communication network according to one or more network standards and/or demodulates data received over a communication network according to one or more network standards.

In operation, detection device 100 may be exposed to an analyte such as a chemical compound. Upon exposure to the analyte, the catalyst of catalyst layer 140 may undergo a chemical reaction with the analyte, which may be an endothermic or exothermic reaction. Microheater layer 130 is exposed to any temperature change from the chemical reaction and demands increased power to maintain the setpoint temperature in response to an endothermic reaction and demands less power to maintain the setpoint temperature in response to an exothermic reaction at a rate related to the temperature change caused by the chemical reaction with the analyte that the detection device has been exposed to.

Figure 2:
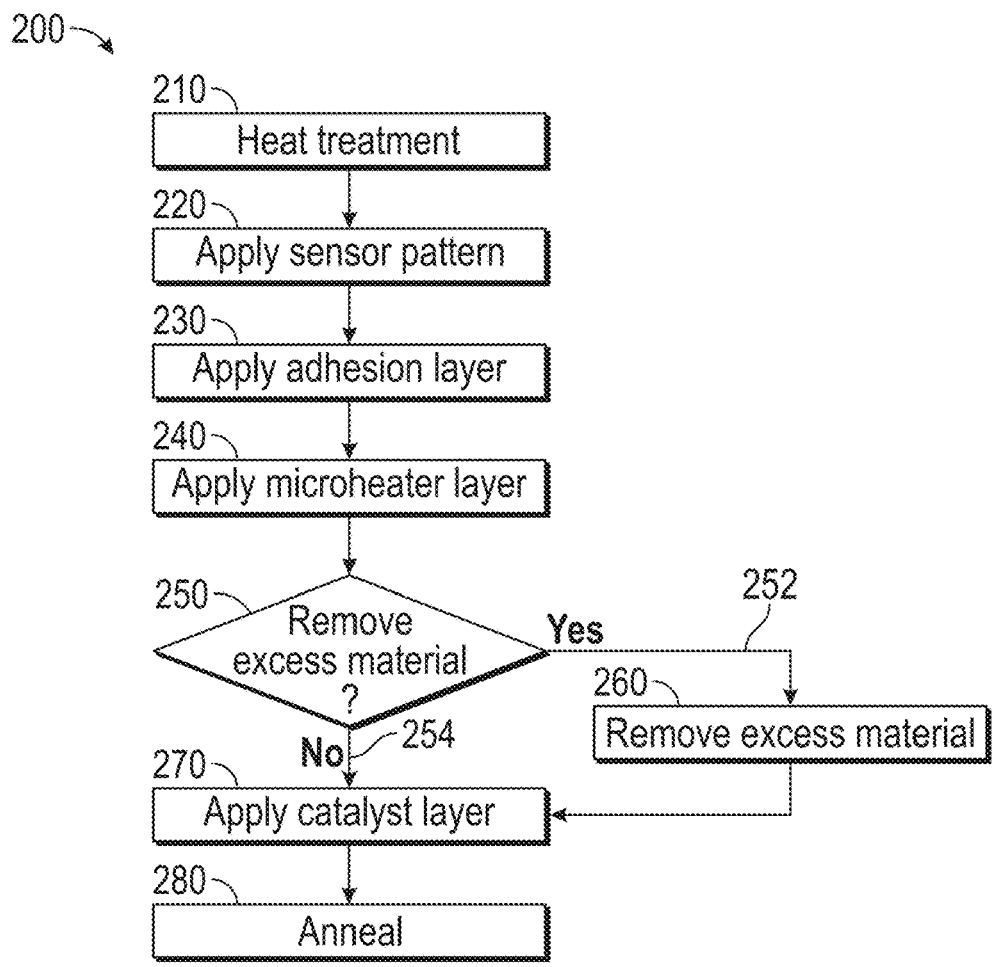
FIG. 2 shows a flowchart describing an exemplary fabrication procedure of an ultrathin vapor sensor.

Method 200 of forming an ultrathin vapor sensor in accordance with the present invention is illustrated in FIG. 2. The heat treatment step 210 involves heat treating a substrate. In preferred embodiments, the substrate is a YSZ substrate and the heat treatment occurs in ambient air at an elevated temperature (e.g., 1000° C.) over a period of time (e.g., three hours). In some embodiments, it may be unnecessary to heat the substrate. For example, an aerogel substrate does not need to be heated. At step 220, a sensor pattern is applied to the substrate in preparation for an adhesion layer. The pattern is preferably applied using photolithography or shadow masking, but it will be appreciated that other known techniques may be utilized. In preferred embodiments, the pattern includes a serpentine region in which portions of the pattern's path may remain close to other portions of the pattern's path. The pattern may be sinusoidal, zig-zag, irregular, a series of straight or curved segments, or other configuration that may be desired based on heat transfer characteristics, aesthetics, or other desirable characteristics. The adhesion layer is applied at step 230. Preferably, the adhesion layer is formed of a material such as copper applied at a thickness (e.g., 400 angstroms) over the thermodynamic sensor pattern. The adhesion layer may be applied using sputtering, evaporation, or other known techniques. At step 240, the metallic microheater layer is applied. In preferred embodiments, the microheater layer is formed of palladium and is applied at a thickness (e.g., 1 micrometer) over the pattern. Step 250 provides an optional decision as to whether it is desirable to remove excess material. If it is not desired, the method proceeds along path 254 to step 270. If it is desirable to remove excess material, such as if photolithography is utilized, then the method proceeds along path 252 to the step 260 wherein the extra material is removed. In some embodiments, optional step 260 involves lifting off excess copper and palladium metallization, leaving the remaining palladium-based sensor adhered to the YSZ substrate. Step 260 continues to step 270, wherein the catalyst layer is applied. In some preferred embodiments, a metal oxide catalyst is applied in a layer having a thickness (e.g., 1.2 micrometers) over the serpentine region of the palladium sensor. Proceeding to step 280, annealing is performed. In preferred embodiments, the copper-based microheater and palladium-based sensor are annealed at a temperature (e.g., 500° C.) for a period of time (e.g., 30 minutes) in a nitrogen atmosphere.

In developing embodiments of ultrathin vapor sensors in accordance with the present invention, a number of problems were identified and overcome. For example, YSZ substrates and palladium microheaters were found to exhibit different coefficients of thermal expansion (CTE), which led to poor adhesion as the sensor was heated and cooled during operation. This lack of adhesion was mitigated by sputter-coating a 400-angstrom thick copper adhesion layer in step 230. The copper adhesion layer was sputter-coated in the windows of the photoresist prior to deposition of the palladium microheater. Unlike known thermodynamic sensing platforms, the ultrathin vapor sensor does not require an $Al_2O_3$ passivation layer between the catalyst and the sensor. Removal of this layer further reduced the thermal mass by orders of magnitude relative to the alumina coatings employed in previous solid-state sensors which comprised an alumina cement layer with a thickness on the order of hundreds of micrometers. The excessive thermal mass associated with the alumina cement caused significant heat loss to the substrate, i.e., significant amounts of heat were dissipated before reaching the catalyst surface, thus producing a temperature gradient between the microheater and the catalyst surface. Removal of this passivation layer not only reduced the thermal mass of the sensor but also more effectively controlled the temperature of the catalytic layer, thereby improving the thermal resolution of the measurement when the catalyst interacted with an analyte. The catalyst layer preferably is a 1.2 µm thick metal oxide catalyst layer. As previously mentioned, a variety of catalysts have been experimentally investigated for this purpose. Each of these thin-film materials were sputter-coated onto the thin film resistor and optimized for thickness to maximize catalytic sensitivity while maintaining the low mass characteristics of the microheater. Overall, embodiments of the fully fabricated microheater comprise a thickness of approximately 21.6 micrometers.

Figure 3:
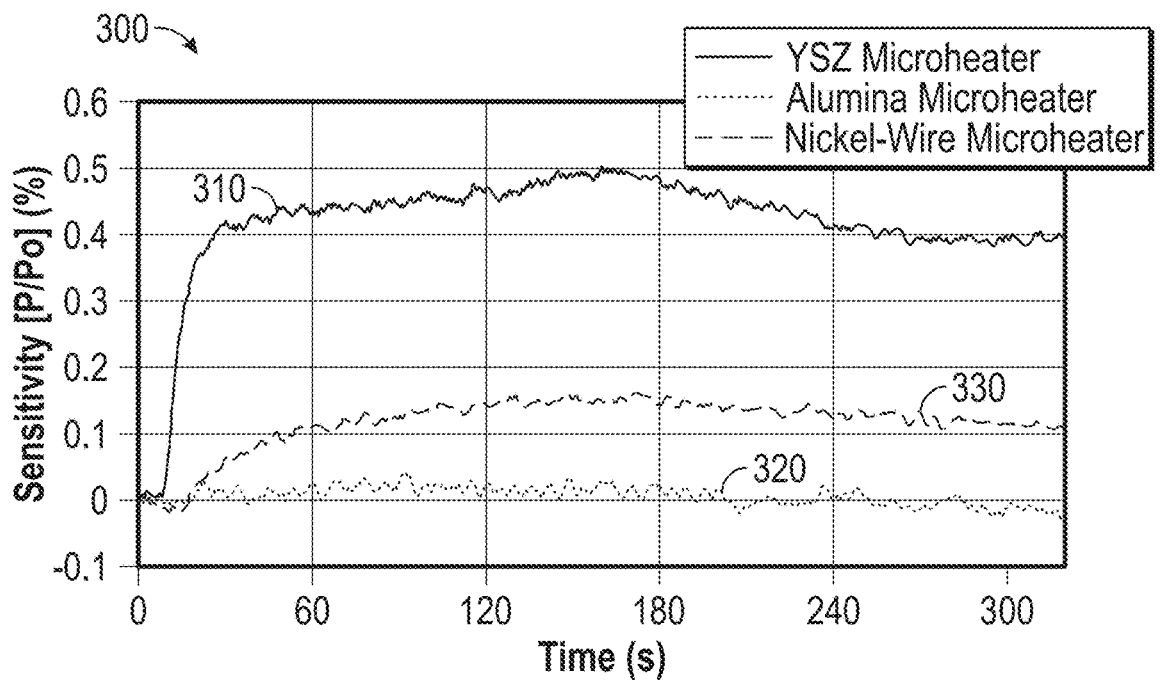
FIG. 3 shows an illustrative graphical representation of a comparison between the response of an ultrathin (YSZ-based) vapor sensor, an alumina-based sensor, and a free-standing nickel wire sensor to 20 ppm TATP using an operating temperature of 175° C.

A comparison of different sensors is made in reference to FIG. 3. As illustrated, FIG. 3 depicts comparison 300 between the sensitivity results of an YSZ-based embodiment of ultrathin vapor sensor 310 to both alumina-based sensor 320 and free-standing Ni-wire sensor 330. Each sensor platform employed a SnO catalyst and the target gas was 20 ppm triacetone triperoxide (TATP). The ultrathin vapor sensor utilizing the ultrathin YSZ substrates outperformed the Ni-wire microheaters in terms of both sensitivity and response time, e.g., the alumina-based sensor appeared unresponsive due to the relatively large operating powers required for heating (2-3 W). The ultrathin (YSZ-based) vapor sensor displayed a sensitivity of 0.45%, which is 2.5 times greater than the sensitivity of the free-standing Ni-wires. Additionally, the response time decreased significantly, which allowed real-time detection of the molecules of interest. The t10 response time of the YSZ-based sensor was approximately 10 seconds, which is significantly faster than the previous platforms (25 seconds for the alumina-based sensors and 17 seconds for the Ni-wire sensors). These results were attributed to a reduction in thermal mass with no corresponding sacrifice in the catalyst surface area.

Figure 4B:
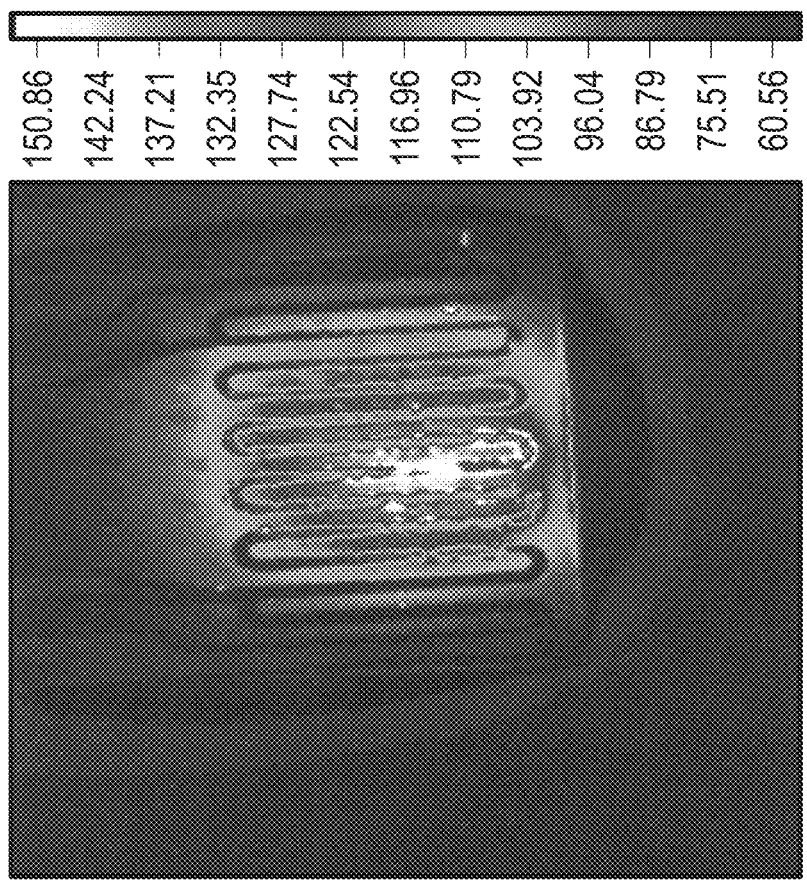
FIG. 4B shows a high-resolution IR image of an ultrathin (YSZ-based) vapor sensor employing a Ni microheater using an operating temperature of 175° C.
Figure 4A:
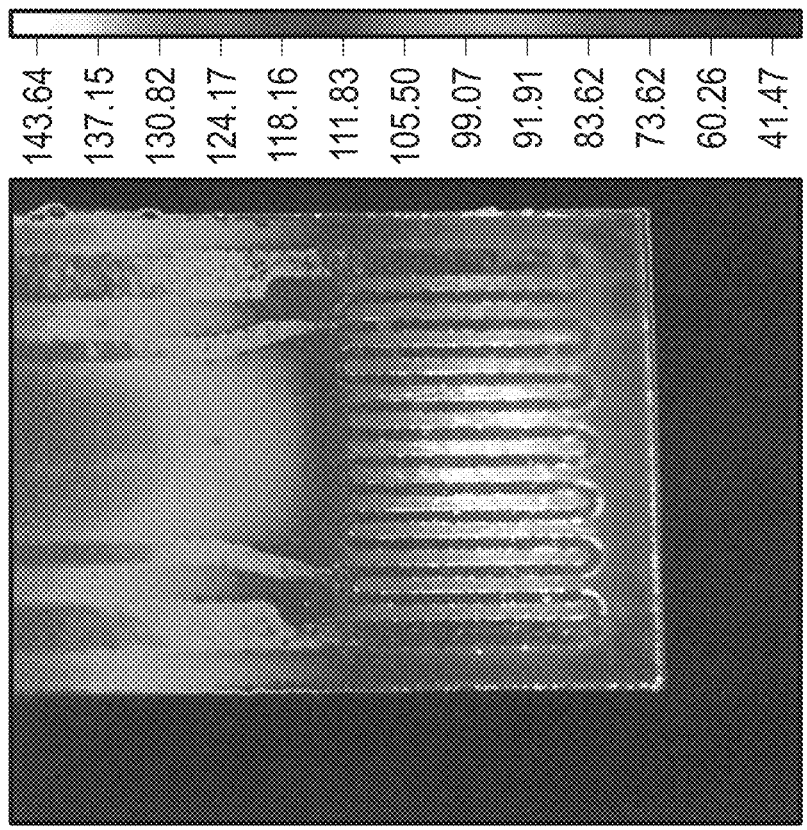
FIG. 4A shows a high-resolution IR image of a 1 mm thick alumina-based sensor employing a Ni microheater using an operating temperature of 175° C.

FIG. 4A depicts a high-resolution infrared (IR) image of a 1 mm thick alumina-based sensor, whereas FIG. 4B depicts a high-resolution IR image of an ultrathin (YSZ-based) vapor sensor. These figures illustrate the above-mentioned findings that the ultrathin YSZ substrate exhibits highly localized heating in the "z" direction when compared to the alumina based solid-state sensors. The thermal properties were found to be highly anisotropic in that the in-plane thermal conductivity of the YSZ (2.7 W/mK) was significantly lower than that of the alumina (30 W/mK). This difference caused the heat to remain in the area of catalyst without dissipating laterally to the rest of the sensor platform to the degree of the alumina based solid-state sensors. One outcome of this was a significant decrease in the temperature required for detection using the ultrathin vapor sensor, as well as a reduction in the power required to operate the sensor. In comparison, previously-known alumina-based sensors required operating temperatures of 500° C. or greater for the detection of compounds at trace levels. The YSZ-based sensor showed better sensitivity and response times at significantly lower operating temperatures (175° C.), which resulted in a significant decrease in power (400 mW). The YSZ-based microheaters also cooled to room temperature in just seconds after deactivation, thus making the overall duty cycle much shorter in duration. These features permit real-time detection with little to no delay related to sensor recovery.

Figure 5:
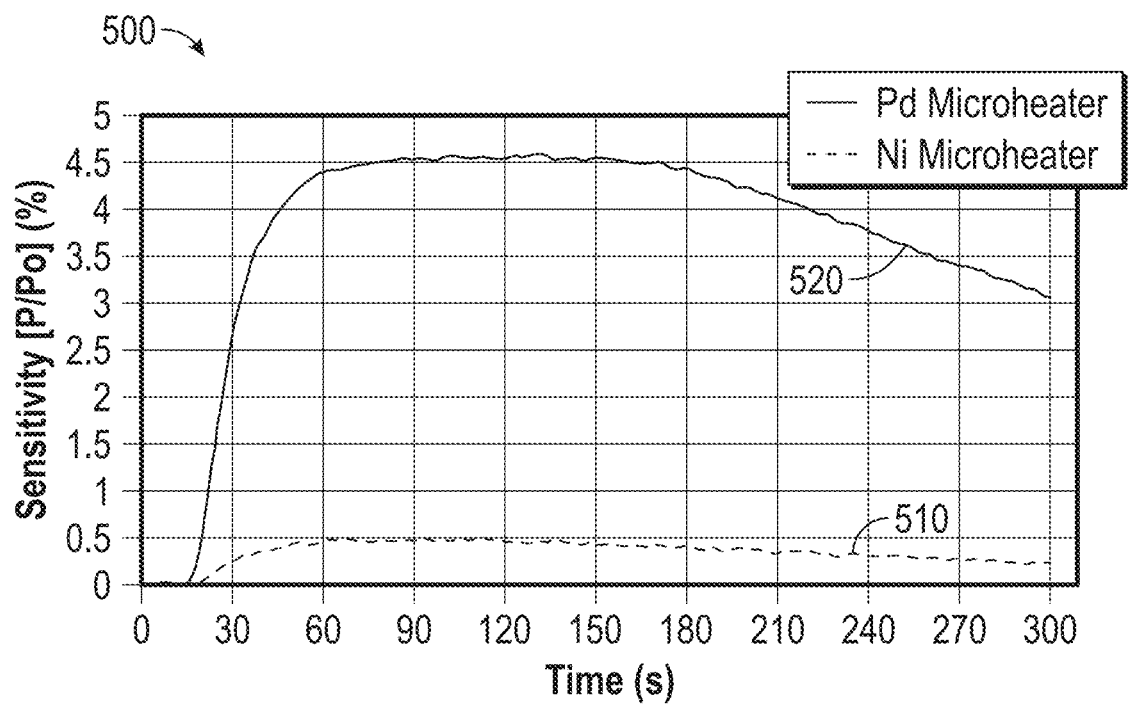
FIG. 5 shows an illustrative graphical representation of a comparison between the responses of two ultrathin (YSZ-based) vapor sensors to 20 ppm TATP. The sensors employed two different microheater metallizations using an operating temperature of 175° C.

Enhanced sensitivity of ultrathin vapor sensor embodiments as compared to known sensors can also be attributed to the implementation of a Pd-based microheater. FIG. 5 depicts comparison 500 between the response of an ultrathin vapor sensor employing a Ni-based microheater 510 and the response of an ultrathin vapor sensor employing a Pd-based microheater 520. The conditions of the comparison include 20 ppm TATP at 175° C. Even though the Pd thin films deposited on the YSZ were thick enough to be continuous, the catalytic properties of the Pd significantly increased the specific response of the SnO catalyst to TATP. The Pd-microheater sensors displayed a sensitivity of 4.5%, which represents an order of magnitude improvement over the Ni-based sensors. Due to the similar power requirements of the Pd-based microheaters (370 mW) and Ni-based microheaters (400 mW), the enhanced sensitivity was attributed to the heat effect observed for the Pd-based microheaters coated with a SnO catalyst. The observed catalytic amplification also reduced the response time of this sensor platform. The t10 response time of the Pd-based microheater was 8.75 s, which represents a substantial decrease relative to the Ni-based platform (10 s).

Figure 6:
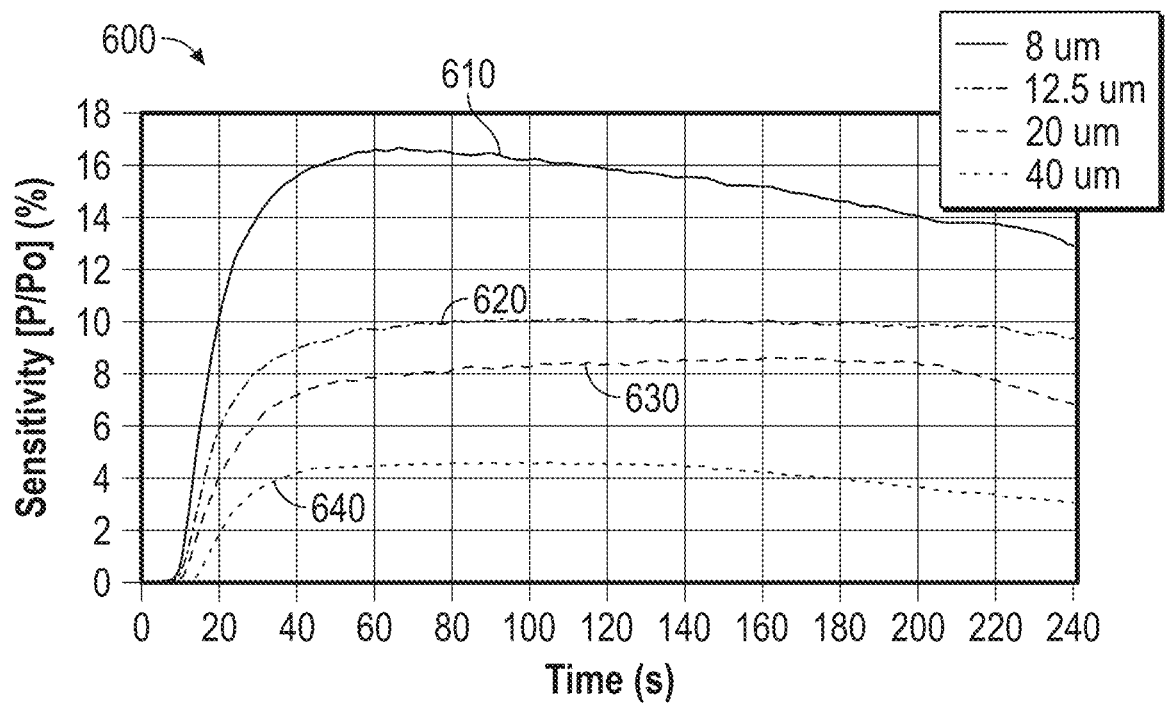
FIG. 6 shows an illustrative graphical representation of a comparison between the responses of four ultrathin vapor sensors fabricated on YSZ substrates of varying thickness to 20 ppm TATP using an operating temperature of 175° C.

Further improved performance of the ultrathin vapor sensor was achieved through the minimization of thermal mass. FIG. 6 depicts comparison 600 of the response times of four ultrathin vapor sensors fabricated on YSZ substrates of varying thicknesses when exposed to 20 ppm TATP. Specifically, comparison was made between results of 8 μm thick YSZ-based sensor 610, 12.5 μm thick YSZ-based sensor 620, 20 μm thick YSZ-based sensor 630, and 40 μm thick YSZ-based sensor 640. Empirical findings revealed that the sensitivity and response time improved as the thermal mass was reduced. Overall, an ultrathin vapor sensor employing 8 μm thick YSZ displayed the highest sensitivity of all sensors (16%), which represents a 30-fold increase in sensitivity over the 40 μm thick YSZ-based sensors. The reduction in thermal mass resulted in significantly lower power requirement as well. At an operating temperature of 175° C., the 8 μm thick YSZ sensors required only about 250 mW to operate, which represents a significant decrease over the 40 μm thick platform (370 mW). Additionally, much shorter response times were achieved through implementation of the 8 μm YSZ sensors, e.g., the Pd-based sensors fabricated on 8 μm YSZ required just 3 seconds to reach 10 percent of the maximum response. This improvement represents a 10-fold decrease over the alumina-based sensors (25 seconds).

Figure 7A:
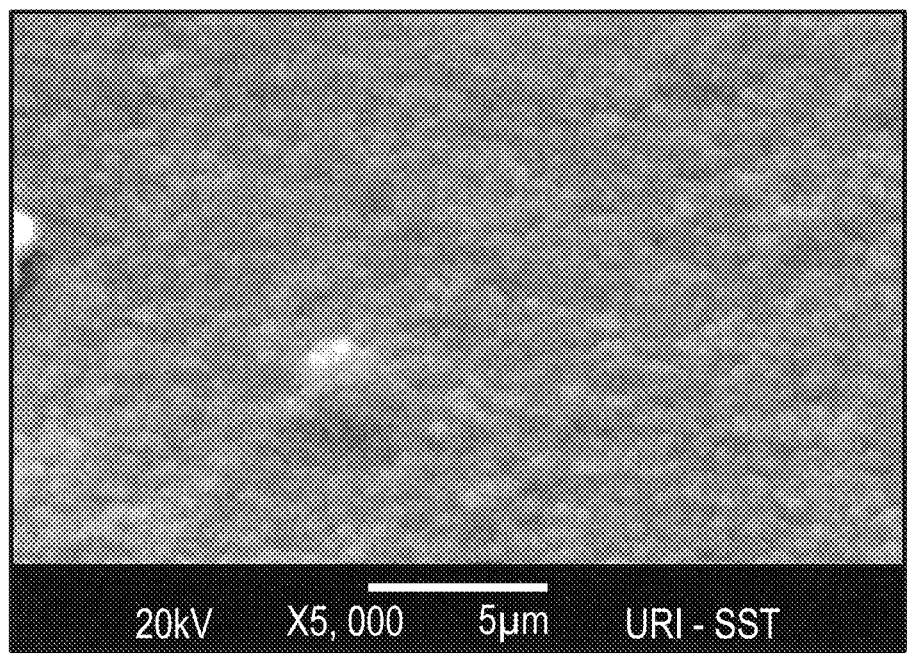
FIG. 7A shows an SEM micrograph of a post-annealed SnO catalyst that was sputtered in 7 mT Ar.
Figure 7B:
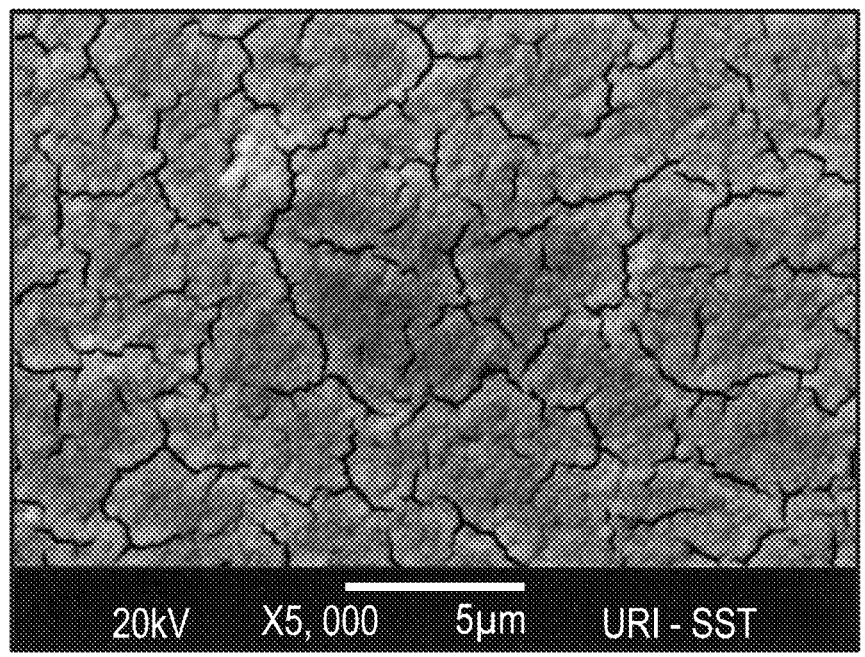
FIG. 7B shows an SEM micrograph of a post-annealed SnO catalyst that was sputtered in 15 mT Ar.

Further optimization of ultrathin vapor sensors in accordance with the present invention was achieved through variation of catalyst porosity. Again, thickness combined with the enhanced catalytic effect associated with the Pd-based microheaters yielded unprecedented sensitivity. Because the ultrathin vapor sensors employ discrete thin films of Pd and SnO, the catalyst porosity played a large role in amplifying the general catalytic properties of the palladium. Porosity in the catalyst was increased by increasing the argon partial pressure during sputtering. Specifically, when the argon partial pressure was increased from 7 mtorr to 15 mtorr, the result was a much greater point defect content (argon trapped in the film). The resulting SnO films were then annealed in nitrogen to release any trapped argon prior to testing. This produced more porosity as the trapped argon diffused out of the film. FIG. 7A depicts a scanning electron microscope (SEM) micrograph of a nitrogen annealed SnO thin film sputtered in 7 mtorr Ar. The resulting film showed typical sputtered protuberances with little porosity. FIG. 7B depicts shows a SEM micrograph of a nitrogen-annealed SnO thin film sputtered in 15 mtorr Ar. This SEM micrograph shows significant microcracking throughout the SnO film, exposing the Pd underneath. These microcracks provide direct access to the Pd-microheater and the TATP vapor, thus permitting simultaneous exposure to the Pd and SnO.

Figure 8:
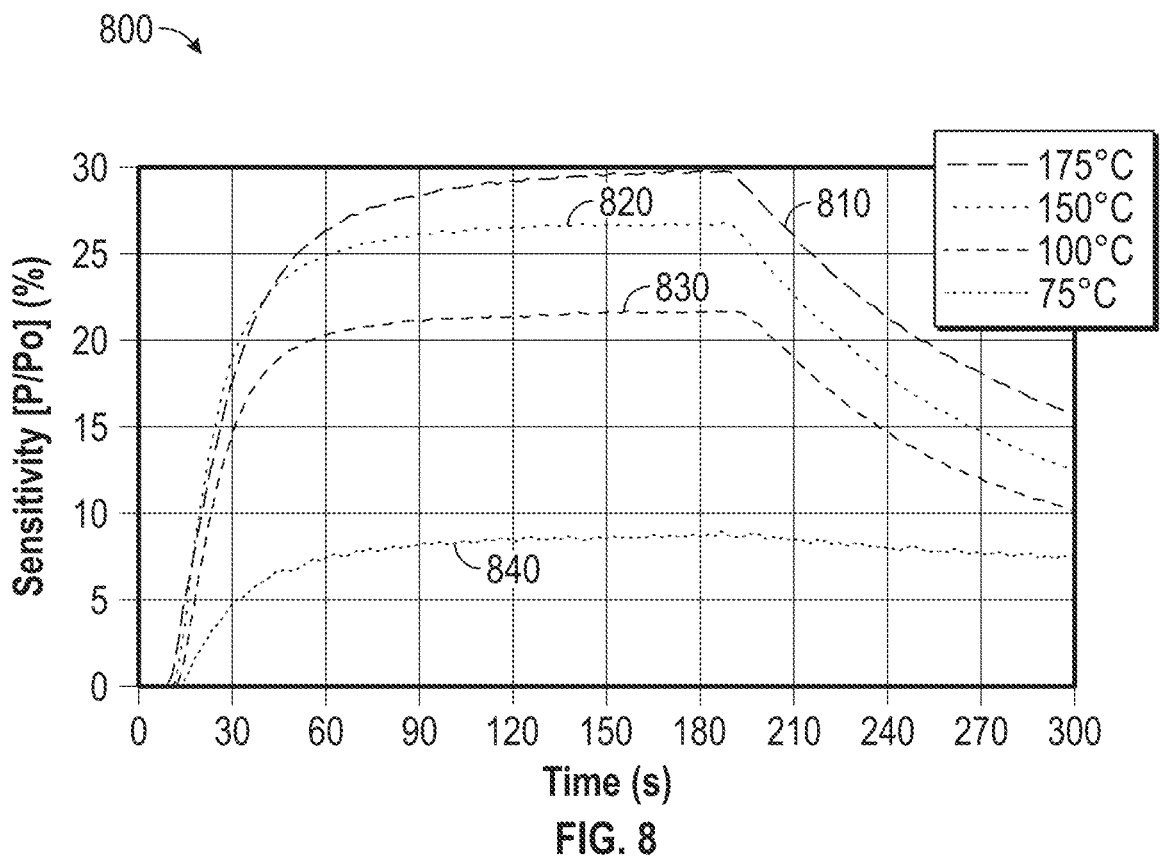
FIG. 8 shows an illustrative graphical representation of a comparison between responses of an ultrathin vapor sensor employing a highly porous SnO catalyst to 20 ppm TATP at a variety of operating temperatures.

FIG. 8 shows comparison 800 of the responses of an ultrathin vapor sensor fabricated on 8 μm YSZ to 20 ppm TATP at a variety of temperatures, specifically 175° C. at line 810, 150° C. at line 820, 100° C. at line 830, and 75° C. at line 840. In the embodiment tested, the sensor showed the best overall sensitivity to TATP. At a temperature of 175° C., the sensor displayed a sensitivity of 30%, which represents a 60-fold increase in sensitivity over the 40 μm YSZ-based platform. In addition, the highly porous SnO catalyst provided greater sensitivity at significantly lower operating temperatures. At 75° C., the sensor displayed a sensitivity of around 9%, which compares favorably to the other YSZ-based platforms. Additionally, the reduction in sensor operating temperature lowered the power requirements significantly so that at 75° C., the sensor required only 150 mW to reach the desired operating temperature. Advantageously, this requirement permits further portability of the sensor platform.

Ultrathin vapor sensors have also been fabricated employing a variety of other metal oxide catalysts. These include aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO). Each catalyst displays different levels of sensitivity and selectivity based on the chemical reactions that result from the interaction with the target analyte.

Figure 9:
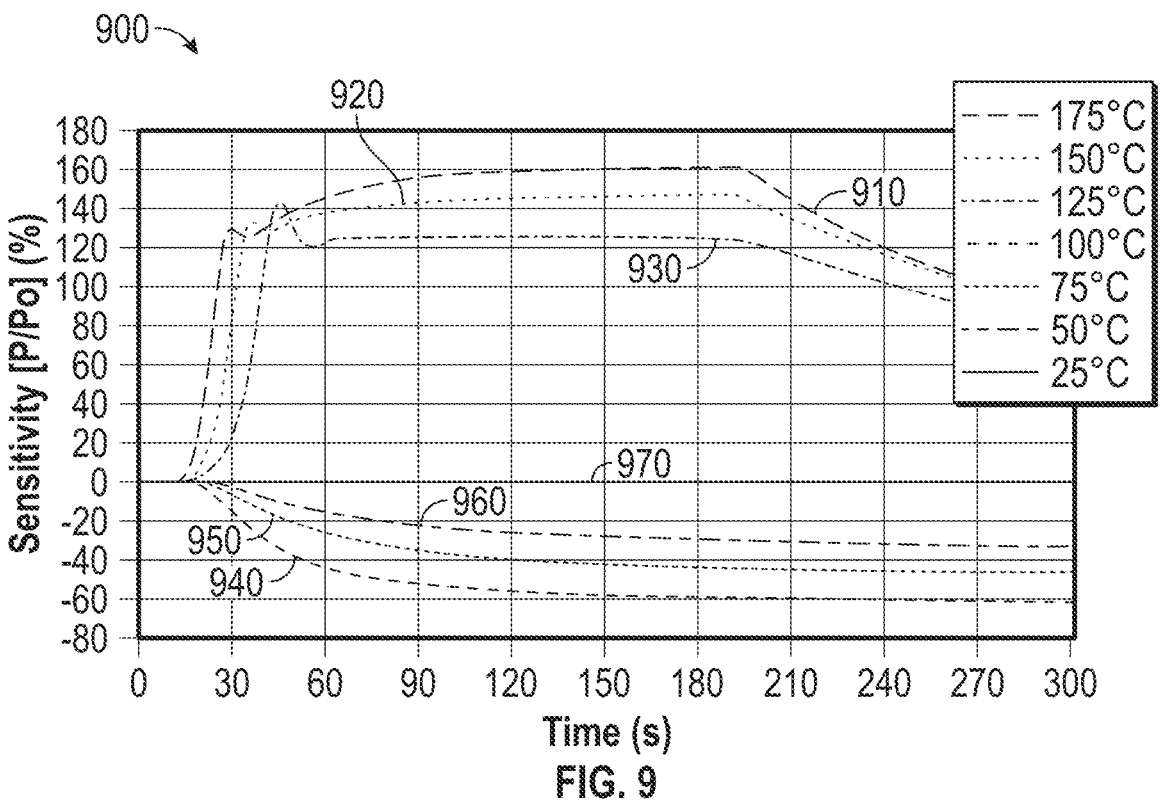
FIG. 9 shows an illustrative graphical representation of a comparison between responses of an ultrathin vapor sensor employing an ITO catalyst to 20 ppm TATP at a variety of operating temperatures.

For example, ITO is a catalyst consisting of highly specific compositions of indium and tin oxide. In reference to FIG. 9, the response of an ultrathin vapor sensor employing a 1.2 μm thick ITO catalyst to 20 ppm TATP at a variety of operating temperatures is described. Specifically, comparison 900 is made between the ultrathin vapor sensor at temperatures of 175° C. at line 910, 150° C. at line 920, 125° C. at line 930, 100° C. at line 940, 75° C. at line 950, 50° C. at line 960, and 25° C. at line 970. At 175° C., the sensor achieved a sensitivity of 160% which represents a 5× increase over a similar sensor employing an SnO catalyst. The sensor also shows improved sensitivity at lower operating temperatures. Based on the properties of the catalyst, at operating temperatures <125° C., the sensor response is negative, which implies that an exothermic reaction has occurred. These reactions release heat resulting in a decrease in required electrical power and thus a negative response. At 100° C., the sensor exhibited a −60% response which is an order of magnitude greater than response exhibited by a SnO catalyst. This improved sensitivity is a result of ITO's high electrical conductivity, which promotes easy transfer of electrons during oxidation and reduction reactions. Catalysts of this type allow for trace detection at the parts-per-trillion (ppt) level using the ultrathin vapor sensors.

Figure 10:
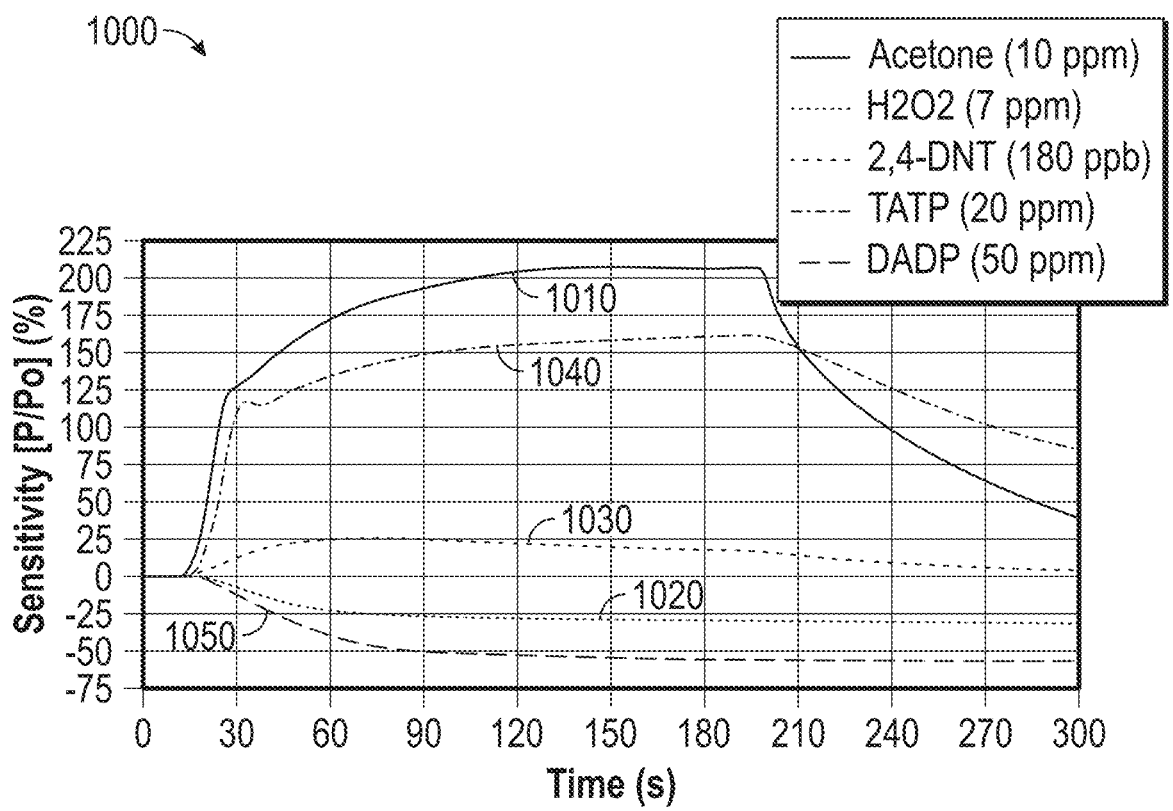
FIG. 10 shows an illustrative graphical representation of a comparison between responses of an ultrathin vapor sensor employing an ITO catalyst to variety of analytes of different vapor pressures at an operating temperature of 175° C.

In addition to unparalleled sensitivity, ITO catalyst also displays improved selectivity. FIG. 10 shows comparison 1000 of responses of an ultrathin vapor sensor employing an ITO catalyst to a variety of analytes, including acetone (10 ppm) at line 1010, $H_2O_2$ (7 ppm) at line 1020, 2,4-DNT (180 ppb) at line 1030, TATP (20 ppm) at line 1040, and diacetone diperoxide (DADP) (50 ppm) at line 1050. Here, the sign and slope of the responses are highly specific toward each analyte. More specifically, ultrathin sensors employing ITO catalysts exhibited a positive (endothermic response) to acetone, TATP, and 2,4-DNT while also exhibiting a negative (exothermic) response to $H_2O_2$ and DADP.

Figure 11:
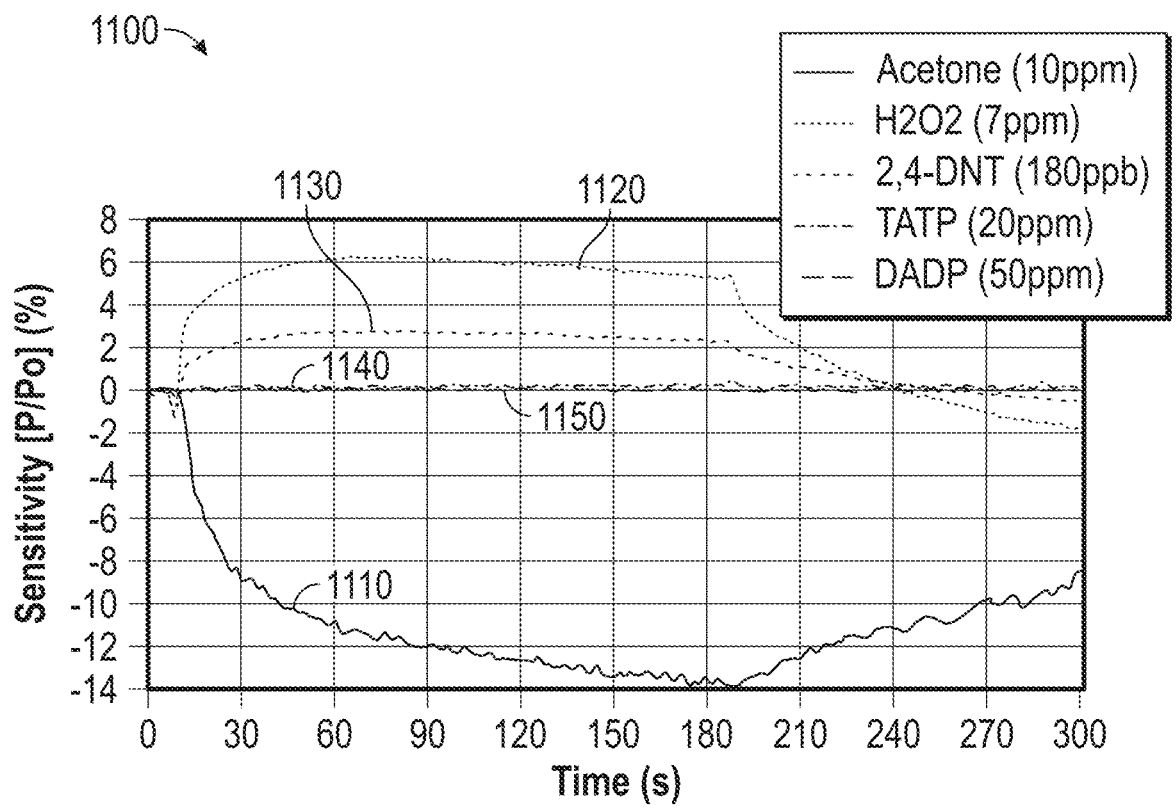
FIG. 11 shows an illustrative graphical representation of a comparison between responses of an ultrathin vapor sensor employing a WO catalyst to variety of analytes of different vapor pressures at an operating temperature of 250° C.

FIG. 11 shows comparison 1100 of responses of an ultrathin vapor sensor employing a WO catalyst to a variety of analytes at an operating temperature of 250° C. The specific analytes are acetone (10 ppm) at line 1110, $H_2O_2$ (7 ppm) at line 1120, 2,4-DNT (180 ppb) at line 1130, TATP (20 ppm) at line 1140, and DADP (50 ppm) at line 1150. Like the ITO catalyst discussed above, WO displays highly selective responses to each analyte. WO shows positive (endothermic) responses to $H_2O_2$ and 2,4-DNT, a negative (exothermic) response to acetone, and is completely inert to TATP and DADP. Similar responses are shown for MnO and $Al_2CuO_4$ (FIGS. 12 and 13 respectively), which are selectivity inert to TATP while also displaying responses to each of the other analytes. These selective responses represent the foundation for a highly selectivity ultrathin vapor sensor array for analyte "fingerprinting."

Figure 12:
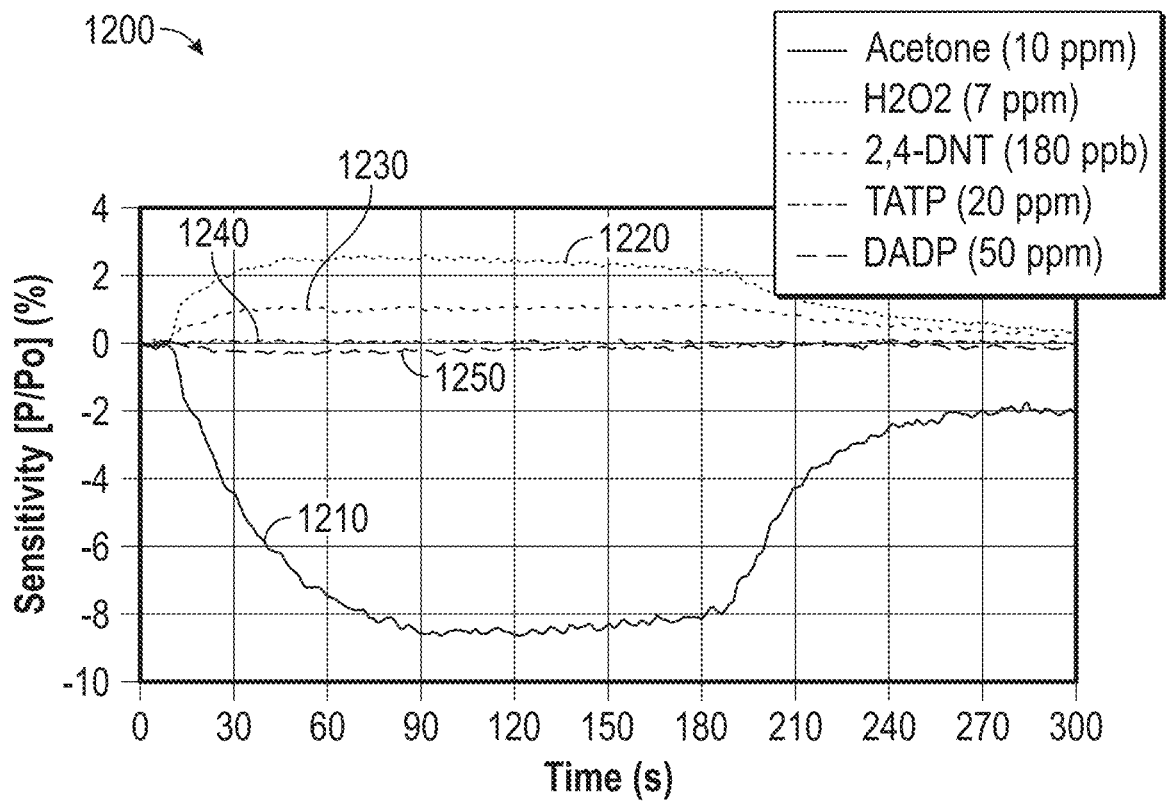
FIG. 12 shows an illustrative graphical representation of a comparison between responses of an ultrathin vapor sensor employing an MnO catalyst to variety of analytes of different vapor pressures at an operating temperature of 250° C.

FIG. 12 depicts comparison 1200 of responses of an ultrathin vapor sensor employing a MnO catalyst to a variety of analytes. The specific analytes are acetone (10 ppm) at line 1210, $H_2O_2$ (7 ppm) at line 1220, 2,4-DNT (180 ppb) at line 1230, TATP (20 ppm) at line 1240, and DADP (50 ppm) at line 1250.

Figure 13:
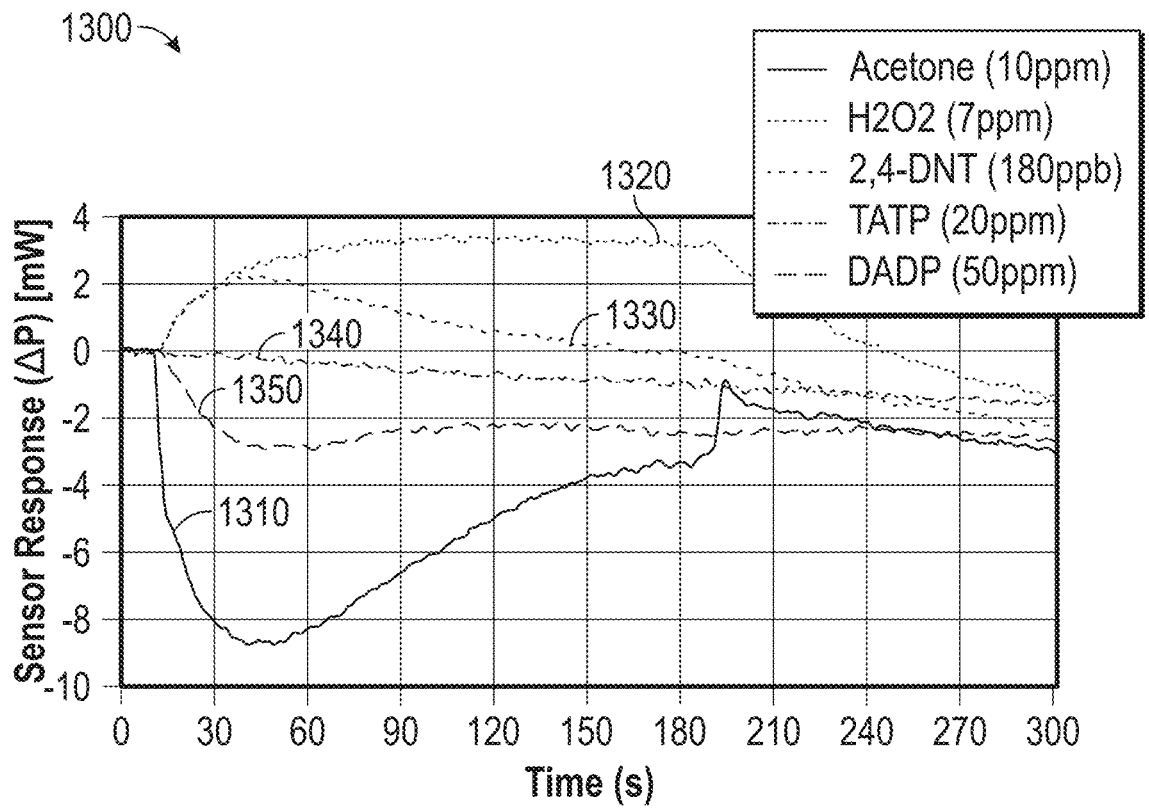
FIG. 13 shows an illustrative graphical representation of a comparison between responses of an ultrathin vapor sensor employing an $Al_2CuO_4$ catalyst to variety of analytes of different vapor pressures at an operating temperature of 250° C.

Likewise, FIG. 13 depicts comparison 1300 of responses of an ultrathin vapor sensor employing a $Al_2CuO_4$ catalyst to a variety of analytes. The specific analytes are acetone (10 ppm) at line 1310, $H_2O_2$ (7 ppm) at line 1320, 2,4-DNT (180 ppb) at line 1330, TATP (20 ppm) at line 1340, and DADP (50 ppm) at line 1350.

Figure 14A:
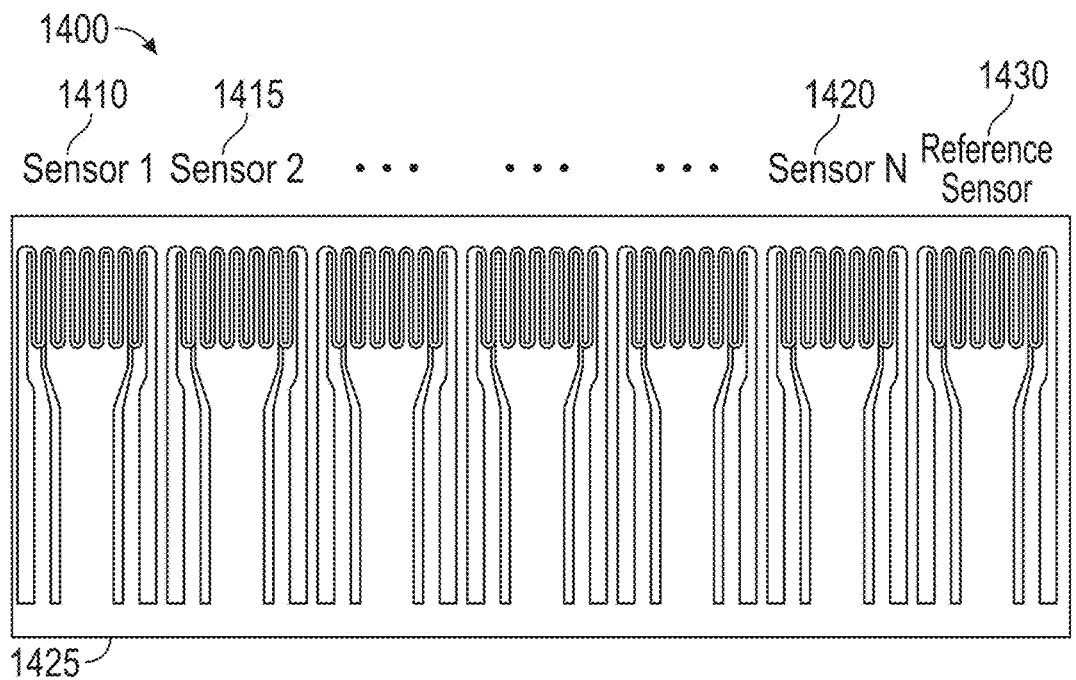
FIGS. 14A and 14B depict embodiments of sensor arrays in which the substrate is shared by the sensors and in which each sensors has an individual substrates, respectively.

Ultrathin vapor sensors in accordance with the present invention are well-suited for an array platform capable of selective detection and identification of a library of vapor phase analytes. The highly anisotropic heating properties allow for easy integration of more than ten or more microheaters (including a reference) on a single substrate with no appreciable thermal communication. An array of this type could be quantitative or qualitative depending on the desired application. It will be appreciated that if a plurality of ultrathin vapor sensors share a common substrate, then the individual substrates of each sensor are contiguous with the substrates of the other commonly mounted sensors. FIG. 14A illustrates an embodiment of sensor array 1400 having N sensors and one reference sensor. Specifically, first sensor 1410, second sensor 1415, and other sensors up to and including Nth sensor 1420 are all mounted on substrate 1425. Reference sensor 1430 is also mounted on substrate 1430.

Figure 14B:
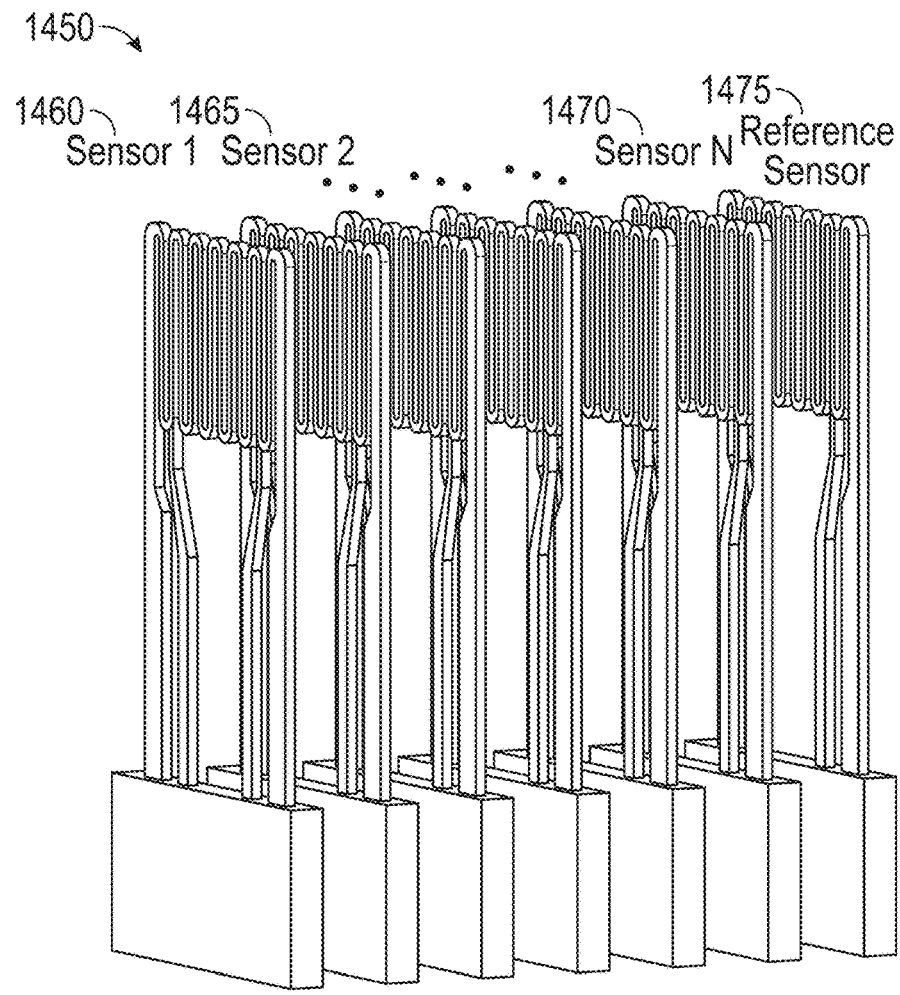

In other preferred embodiments, ultrathin vapor sensors comprise a plurality of microheaters that do not share a common substrate. For example, a device may include a plurality of microheaters (including a reference), each with its own substrate to further prevent thermal communication. FIG. 14B illustrates an embodiment of sensor array 1450 having N sensors and one reference sensor. Specifically, first sensor 1460, second sensor 1465, and other sensors up to and including Nth sensor 1470, as well as reference sensor 1475 each are mounted on separate substrates. It will be appreciated that in embodiments wherein the sensors do not share a common substrate, advantages include increased configuration options, including the ability to position the sensors in different locations relative to one another and facilitated replacement options wherein a subset of a group of sensors may be replaced with other sensors having the same or different catalysts.

Sensor arrays, such as those depicted in FIG. 14A and FIG. 14B, display remarkable flexibly and may be placed in a variety of orientations and at any distance with significantly reduced thermal communication between sensors as compared to known systems. In practice, the controller of the sensor is used to heat each microheater individually to a pre-determined temperature setpoint. Upon or after reaching the desired setpoint temperature, the catalyst coated sensors and reference sensor are exposed to a target analyte, preferably this exposure occurs approximately simultaneously. The individual redox reactions on the surface of each catalyst results in heat effects which are determined by the controller based on the power usage of the sensors. Each measurement is then compared to (e.g., subtracted from) the reference measurement to help mitigate any false positives or false negatives. An array of separate sensors, such as those illustrated in FIG. 14B, could be incorporated into a variety of standalone devices including wearables, breathalyzers, scanning wands, etc. Additionally, the low mass and low power requirements facilitates the use of an array of sensors onboard a variety of mobile platforms including drones, robots, and UAVs.

Upon interaction with the target analyte, each catalyst has the potential for three distinct responses. As mentioned above, reduction reactions produce positive (+) responses while oxidation reactions produce negative (−) responses. A catalyst may also be unresponsive to a target analyte, indicating the absence of any catalytic decomposition/redox reactions and thus, no response (NR). A "fingerprint" may be constructed for each target analyte based on the response of each catalyst. Thus, a set of pre-determined catalysts can be chosen to allow "selective" identification of each analyte.

The sensor arrays depicted in FIG. 14A and FIG. 14B, like other embodiments disclosed herein, may be configured to be quantitative and qualitative as desired. In another embodiments, sensor arrays can measure the magnitude of each thermodynamic response and provide real-time measurement of the analyte concentration in addition to rapid identification of the analyte.

Figure 15:
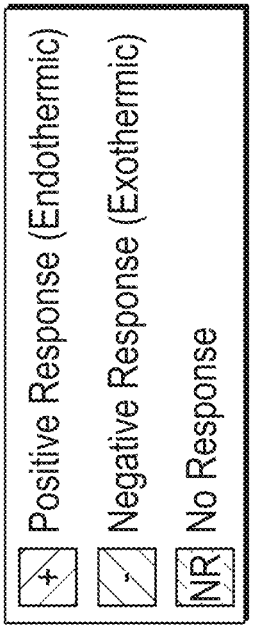
FIG. 15 shows a summary table consisting of the thermodynamic sign indicative of the measured redox reactions, for 12 distinct catalysts making up an ultrathin vapor sensor array.

FIG. 15 shows summary table 1500 containing the thermodynamic sign (positive or negative), and thus an indication of the measured redox reactions, for 12 distinct catalysts making up an embodiment of an ultrathin vapor sensor array. The table shows that each of the five analytes (acetone (10 ppm), $H_2O_2$ (7 ppm), TATP (20 ppm), DADP (50 ppm), and 2,4-DNT (180 ppb)) possess distinct "fingerprints" when the reaction results for each of the 12 sensors are compared, and these "fingerprints" may be used for rapid identification. Thus, an ultrathin vapor sensor array formed using some or all of the catalysts in table 1500 could be used to detect an analyte and could identify which of the five analytes was present based on a determination of whether the reaction at individual sensors was endothermic or exothermic and a comparison of the results of the catalysts to the data in summary table 1500. The data in FIG. 15 may be stored in a database accessible by the controller of a sensor array, and the sensor array may compare heat effects of its sensors to the database of known reaction results in order to identify the existence and/or concentration of an analyte. Such as database of reactions results of different catalysts may include an identification of essential and optional catalysts that promote further flexibility of the sensor array platform by allowing configuration to detect one or more specific analytes, such as a group of analytes associated with explosives. The essential catalysts allow for easy identification of the target analyte while the optional catalysts can be added or removed for redundancy. It will be appreciated that the data of summary table 1500 could be expanded through further testing with numerous analytes and the addition of other potential catalysts. Thus the data in the database of summary table 1500 is not limited to the catalysts or analytes identified therein.

Figure 16:
FIG. 16 shows a summary table consisting of the thermodynamic sign indicative of the measured redox reactions, for six catalysts making up an ultrathin vapor sensor array.

The sensor array platform is unique in that the quantity and composition of the catalysts can be modified based on the desired application. In some embodiments, the sensor array can be configured for the detection of explosives and explosive precursors. For example, FIG. 16 depicts table 1600 with data from a database presented in a tabular form illustrating reaction results of a sensor array having of six catalyst sensors (namely, $Al_2CuO_4$, $Fe_2O_3$, ITO, MnO, SnO, and WO). Sensor arrays including these six catalysts are well-suited for selectively identifying analytes having unique "fingerprints" that are identified as being one of least five explosives and two explosive precursors. The number of detectable explosives may be selectively increased through further testing and the addition of more sensors having different catalysts. Sensor arrays that include the catalysts identified in FIG. 16 may be deployed onboard a variety of wearables, vehicles (cars, drones, UAVs), and robots to detect explosives in airport, train station, subway, warzone, stadium, government building, shopping mall, school, etc. or any densely populated venues.

In other embodiments, sensor arrays may be configured for the detection of drugs and narcotics as well as hallucinogenic and non-hallucinogenic compounds. FIG. 17 depicts table 1700 with data from a database presented in tabular form illustrating reaction results of a sensor array having six catalysts (namely $Al_2CuO_4$, $Fe_2O_3$, ITO, CuO, SnO, and WO). Sensor arrays that include sensors having these catalysts are well-suited for selectively identifying and differentiating between fentanyl, THC, and CBD, each with unique "fingerprints" as compared to the reaction results with the identified catalysts. Additionally, embodiments of a sensor array having the catalysts identified in FIG. 17 have been shown to detect other drugs (e.g., cocaine) and numerous cannabinoids present in marijuana. Sensor arrays including the catalysts identified in FIG. 17 are well-suited to be deployed by law enforcement in breathalyzers for the detection of THC, as well as by border patrol officers in a scanning wand for the identification of drugs and other illicit materials.

In yet other embodiments, sensor arrays may be configured for the detection of biomarkers for known biological functions. FIG. 18 depicts table 1800 with data from a database presented in tabular form illustrating reaction results of a sensor array having six catalysts (namely $Al_2CuO_4$, $Fe_2O_3$, ITO, MnO, SnO, and WO). Sensor arrays that include sensors having these catalysts are well-suited for selectively identifying and differentiating between glucose, fructose, ammonia and $H_2O_2$, thereby providing beneficial diagnostic applications. Glucose vapor has been correlated to blood glucose at known concentrations. Thus, sensor arrays having a configuration of sensors as indicated in FIG. 18 may be deployed as part of a wearable or as a breathalyzer allowing for noninvasive glucose measurement for diabetics. Similarly, ammonia is a known biomarker for chronic kidney disease (CKD). Thus, sensor arrays having a configuration of sensors as indicated in FIG. 18 may be used as part of a breathalyzer for rapid, real-time diagnosis. Moreover, $H_2O_2$ is present is wounds during the healing process. A bandage employing a sensor array having the six catalysts identified in FIG. 18 may measure $H_2O_2$ levels in the wound and provide real-time monitoring of wound healing for first responders.

Figure 19:
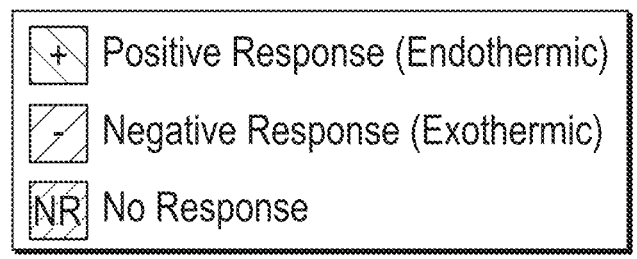
FIG. 19 shows a summary table consisting of the thermodynamic sign indicative of the measured redox reactions, for six catalysts making up an ultrathin vapor sensor array.

In yet another embodiments, sensor arrays may be configured for the detection of volatile organic compounds (VOCs) and other industrial compounds. FIG. 19 depicts table 1900 with data from a database presented in tabular form illustrating reaction results of a sensor array having six sensors each with one of the following catalysts: $Al_2CuO_4$, $Fe_2O_3$, ITO, MnO, SnO, and WO. Sensor arrays with such a configuration are well-suited for selectively identifying and differentiating between natural gas, acetone, and methanol. Such sensor arrays may be used, for example, as part of a stationary system for the detection of natural gas leaks in homes and industrial settings.

The tables shown in FIGS. 15-19 depict qualitative examples of data from one or more databases of reaction results of various analytes when exposed to sensors having different catalysts. Such data, when used with a sensor array having sensors with pre-selected catalysts, may be used for the selective identification of analytes by the thermodynamic sensor array. It will be appreciated that the data results identified in these tables represents only a sample of the data collected and that additions to the database may be made through further testing with additional analytes and/or sensors having other catalysts. The tables of FIGS. 15-19 also represent data that may be used (and expanded on) as part of a database for a sensor platform capable of detecting selected analytes.

It will be appreciated that some embodiments of a sensor array may be special purpose detection devices having sensors with catalysts that are selectively chosen to target one or more analytes falling within a certain category (e.g., explosives, drugs and narcotics, biomarkers, etc.). Likewise, other embodiments may contain a larger number of sensors and may be capable of serving as a general purpose detection device, wherein the device may be capable of detecting and differentiating between analytes from a plurality of categories.

Figure 20:
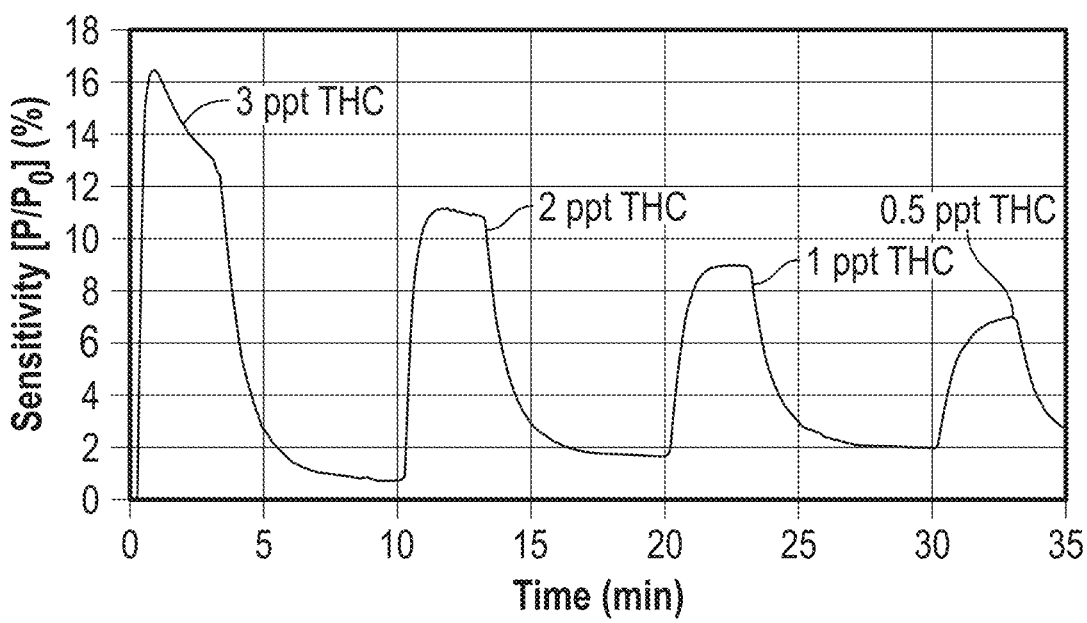
FIG. 20 shows an illustrative graphical representation of the response of an ultrathin vapor sensor to tetrahydrocannabinol (THC) at a variety of concentrations using an operating temperature of 175° C.
Figure 21:
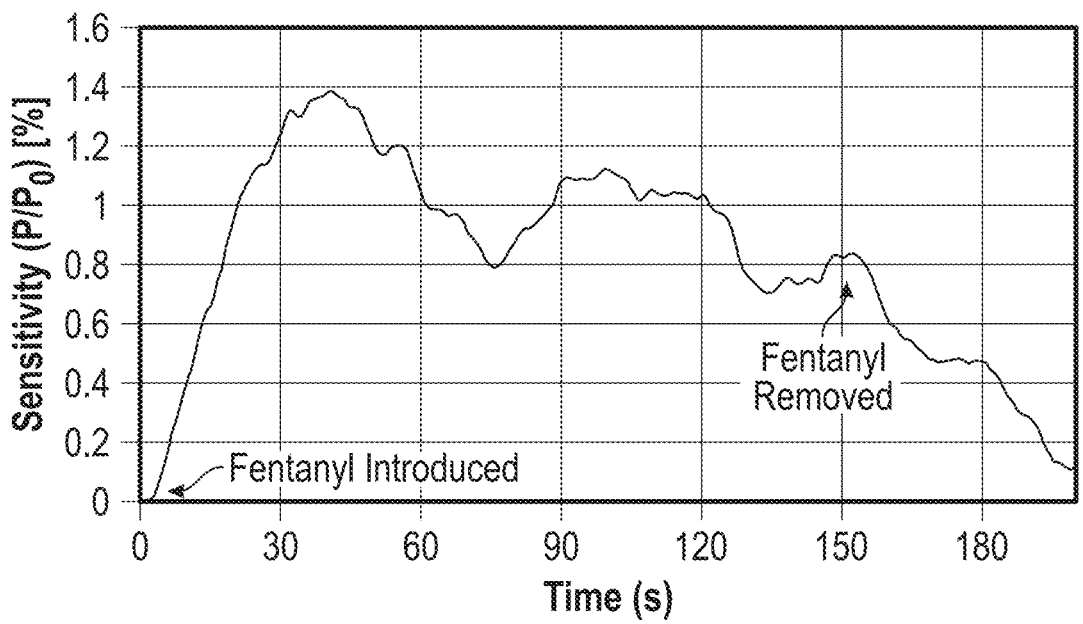
FIG. 21 shows an illustrative graphical representation of the response of an ultrathin vapor sensor to 11 ppt fentanyl using an operating temperature of 175° C.

As mentioned above, the enhanced sensitivity of ultrathin vapor sensor allows for the detection of numerous chemical compounds including explosives, narcotics, pharmacological, and biological compounds. FIG. 20 and FIG. 21 show the response of an ultrathin vapor sensor to tetrahydrocannabinol (THC) and fentanyl respectively. As discussed in reference to FIG. 20, ultrathin vapor sensors of the present invention are capable of detecting THC in the low part-per-trillion levels. One of skill in the art will appreciate that ultrathin vapor sensors disclosed herein could be employed in a variety of law-enforcement or commercial applications for measuring THC levels in a desired search area. This performance has been validated for a variety of vapor phase analytes, as mentioned above. Thus, calibration curves for either increasing or decreasing concentrations may be generated for the precise measurement of the concentration of a target molecule (or analyte) concentration in the vapor phase.

Similarly, as discussed in reference to FIG. 21, ultrathin vapor sensors of the present invention are capable of detecting fentanyl at the ppt level. Accordingly, those of skill in the art will appreciate that these devices allow for real-time, continuous detection of narcotics along borders or other ports-of-entry.

Figure 22:
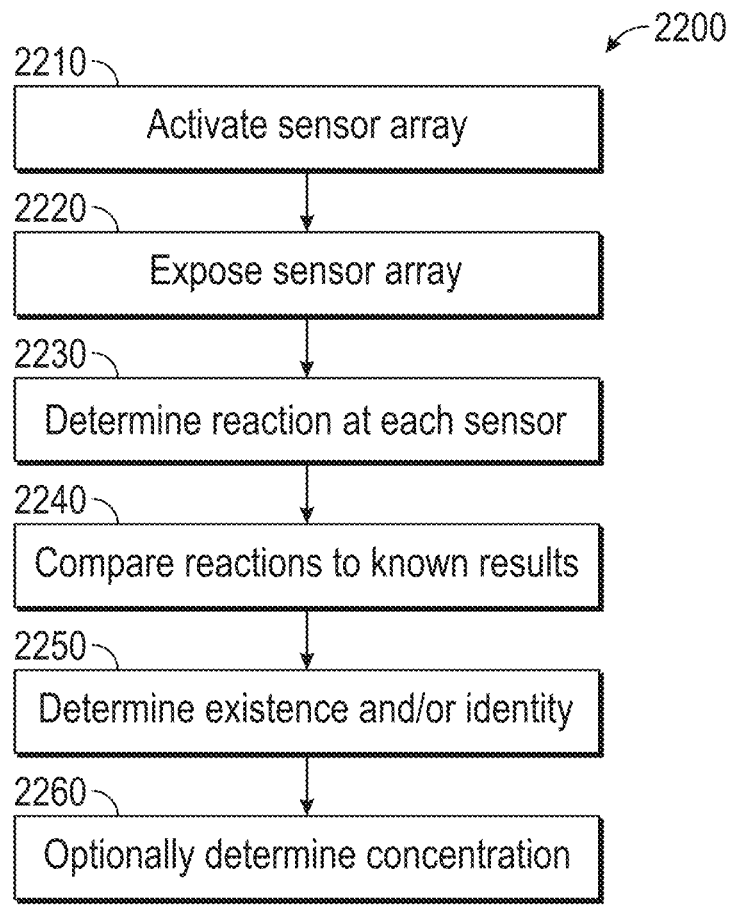
FIG. 22 shows an example of a method of using a sensor array to detect an analyte.

An example of a method of using an embodiment of a sensor array is described in reference to FIG. 22. Method 2200 may be used to determine the existence and/or identity of an analyte and, optionally, the concentration of an analyte. Method 2200 begins at step 2210 in which a user has a sensor array, such as sensor array 1400 or sensor array 1450, each with multiple sensors. The sensor array is activated by providing power to each of the sensors (including one or more reference sensors) so that the temperature of the microheater of each sensor is raised to the desired setpoint temperature. It will be appreciated that each of the sensors need not have the same temperature setpoint, and in operation the sensor array may include sensors operating at different temperature setpoints. In some embodiments, in which the sensors have different setpoint temperatures, a plurality of reference sensors may be provided wherein a reference sensor may be provided for each of the different temperature setpoints and used as a reference point for the sensors having corresponding temperatures. As described herein, the temperature of the sensor may be adjusted through the delivery of power, wherein the addition of power increases the temperature, while the reduction of power lowers the temperature. At step 2220, the sensor array is exposed to an environment in which knowledge of the existence, identity, or concentration of an analyte is desired. For example, the sensor array may be attached to a drone and flown in a battlefield, or mounted in a fixed location at an airport, or provided on a mobile platform that may be worn by or carried by a user. The sensor array could also be carried by a wand extending from the sensors that could be used to "sniff" clothing and personal belongings at a location where security is desirable, e.g., an airport, train station, subway, warzone, stadium, government building, shopping mall, school, etc. When the sensor array is provided in such an environment in which an analyte is present, the analyte reacts with one or more of the sensors in the array.

At step 2230, the reaction at each of the sensors is determined. An exothermic reaction at a sensor will produce heat and the corresponding power required to maintain the sensor at the setpoint temperature will be reduced. Likewise, in response to an endothermic reaction, more power will have to be provided to the sensor to maintain the setpoint temperature. The determination of the reaction at each sensor may be quantitative, in which a determination is made of whether the reaction is endothermic, exothermic, or neither. Additionally, readings of the qualitative magnitude of the power change may be obtained.

At step 2240, the reactions at one or more sensors are compared to known results. In preferred embodiments, the sensor array is in communication with a database of known results and the comparison of the reaction at the sensors to the known results may be automated. At step 2250, a determination is made as to the existence and/or identity of an analyte based on the comparison of the reaction to the known reaction results. For example, consider a sensor array for detecting drugs configured with the six catalysts corresponding to FIG. 17. If the sensor having the ITO catalyst indicates that an endothermic reaction occurred (requiring the addition of electrical power to maintain the setpoint temperature), a determination may be made that CBD, fentanyl, or THC may be present, as each of these produces an endothermic reaction to the sensor with ITO. However, though the results from that single sensor may indicate the presence of a drug, results from additional sensors are required to identify the analyte. For example, if the sensors having the SnO and WO catalysts each indicate an endothermic reaction, whereas the sensors having the $Al_2CuO_4$, $Fe_2O_3$, and CuO sensors each indicate an exothermic reaction, then a determination may be made that the identity of the analyte is THC. It will be appreciated that due to the "fingerprints" of the various analytes, an identification may be made of some analytes by using less than six sensors.

Some embodiments may include optional step 2260, in which a determination is made of the concentration of the analyte. Here, qualitative data is compared to known results. For example, the change in the power provided to the sensors and the amount of that power may be compared to known results to provide an indication of the concentration of the detected analyte. For example, a rapid change in the power required to operate a sensor may be indicative of a higher concentration of the detected analyte, whereas a more gradual change in the required power is indicative of a lower concentration of the analyte. Graphical results demonstrating the differences in speed and intensity associated with various concentrations of THC are shown in FIG. 20. It will be appreciated that a database of known reaction results could have comparable results with other analytes to which sensor results may be compared to for purposes of determining the concentration of the analyte.

Overall, ultrathin vapor sensors employing ultrathin YSZ substrates and Pd-based microheaters display the ability to detect a multitude of compounds in the vapor at trace levels both continuously and in real-time.

In some preferred embodiments, the sensors comprise a Pd-based microheater deposited onto a flexible (<125 μm thick) aerogel substrate, which results in increased sensor sensitivity and selectivity over known devices. Embodiments of a flexible, aerogel-based vapor sensor display minimal thermal mass, which result in high portability with corresponding improvements to the power efficiency. Embodiments of a flexible, aerogel-based sensor have displayed the ability to detect one or more chemical compounds in the vapor phase at trace levels with relatively minimal power requirements. The aerogel substrate described herein preferably possesses high operating temperatures that allow cycling of the sensors between 175° C. and room temperature without decomposition of the aerogel. In some embodiments, the aerogel substrate is fabricated using a polyimide aerogel, such as an aerogel available from Blueshift of Spencer, Massachusetts.

Reducing the thermal mass of the sensing platform by utilizing ultra-lightweight aerogels as the substrate for the thin film microheaters yielded some unexpected results. For example, maintaining catalytic surface area (relative to YSZ-based ceramic sensors) combined with enhanced substrate porosity resulted in the flexible sensor having a lower thermal mass despite an increase in thickness of less than 100 μm. In preferred embodiments of the present invention, the substrates are preferably thin aerogel substrates, such as 85% porosity aerogels having a thickness of between approximately 5 micrometers and 200 micrometers, more preferably between approximately 50 micrometers and 100 micrometers, and most preferably approximately 125 micrometers. The flexible aerogel substrate is preferably porous (85%), so that the majority of the sensor platform is air. This result may be more desirable than results seen with the YSZ substrates used in known solid-state sensors, which are considerably dense. The thermal properties of embodiments of preferred embodiments are highly anisotropic in that the relatively high in-plane thermal conductivity of the aerogel itself (30 W/mK) accounts for only 15% of the substrates overall thermal conductivity. The remaining 85% is a result of air within the aerogel which has a minimal thermal conductivity (0.025 W/mK). Thus, the overall thermal conductivity of the aerogel (4.5 W/mK) compares well to YSZ substrates (2.7 W/mK) at a considerably low thermal mass. This difference causes the heat in flexible vapor sensors to remain in the area of catalyst, similar to known systems employing YSZ substrates. However, as a result of the difference in thermal mass, there is a significant decrease in the temperature required for chemical detection, as well as a reduction in the power required to operate the sensor. For example, detection of compounds in the parts-per-million (ppb) and parts-per-billion (ppt) range is possible at temperatures between 25° C. and 75° C. using embodiments of the flexible vapor sensors. Because more of the thermal energy is focused in the vicinity of the microheater and does not spread to other areas of the substrate as compared to previously-known systems, the resolution of the measurement of the inventive systems is also improved.

Figure 23:
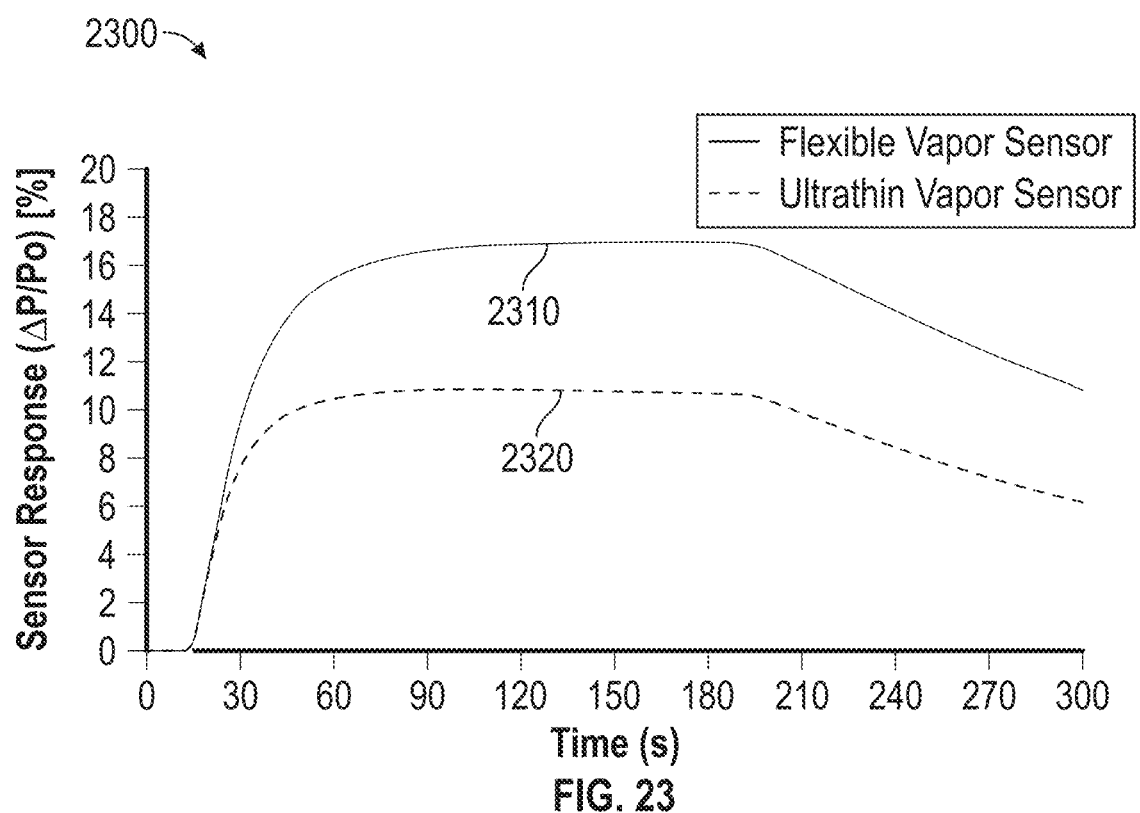
FIG. 23 shows an illustrative graphical representation of a comparison between the response of an ultrathin (YSZ-based) vapor sensor and a flexible (aerogel-based) vapor sensor to 20 ppm TATP using an operating temperature of 175° C.

A comparison of different sensors is made in reference to FIG. 23. As illustrated, FIG. 23 depicts comparison 2300 between the sensor response results of an aerogel-based embodiment of flexible vapor sensor 2310 to ultrathin (YSZ-based) vapor sensor 2320. Each sensor platform employed a SnO catalyst and the target gas was 20 ppm triacetone triperoxide (TATP). The flexible vapor sensor utilizing the preferably porous aerogel substrates outperformed the YSZ-based sensor in terms of both sensor response while displaying similar response times. The flexible (aerogel-based) vapor sensor displayed a sensor response of 17%, which is 1.5 times greater than the sensor response of the ultrathin (YSZ-based) sensor. Additionally, despite the relative increase in substrate thickness (125 μm for the aerogel and 20 μm for the YSZ), the response time remained constant (2 s) These results were attributed to a reduction in thermal mass of the preferably porous aerogel substrate.

Figure 24A:
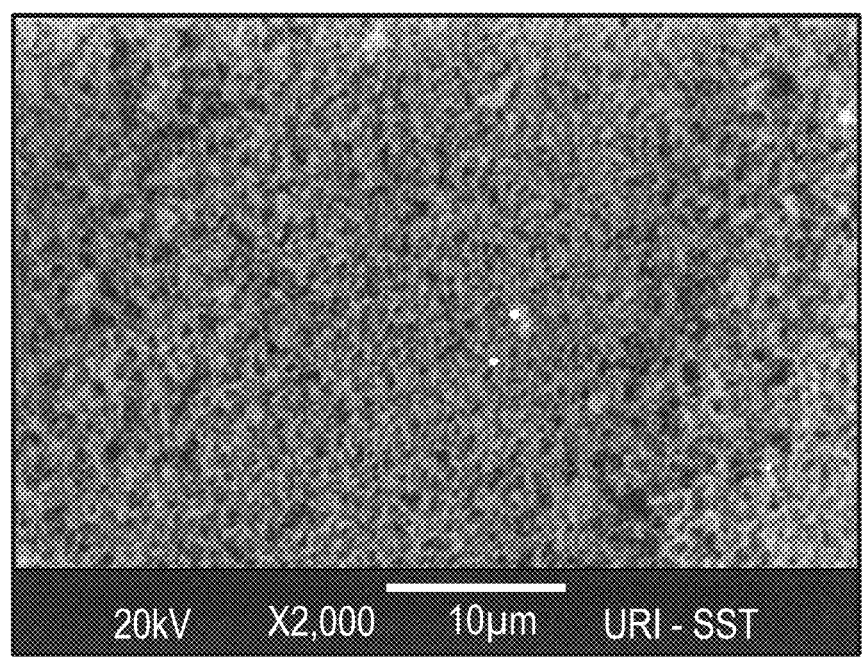
FIG. 24A shows an SEM micrograph of the aerogel substrate surface.
Figure 24B:
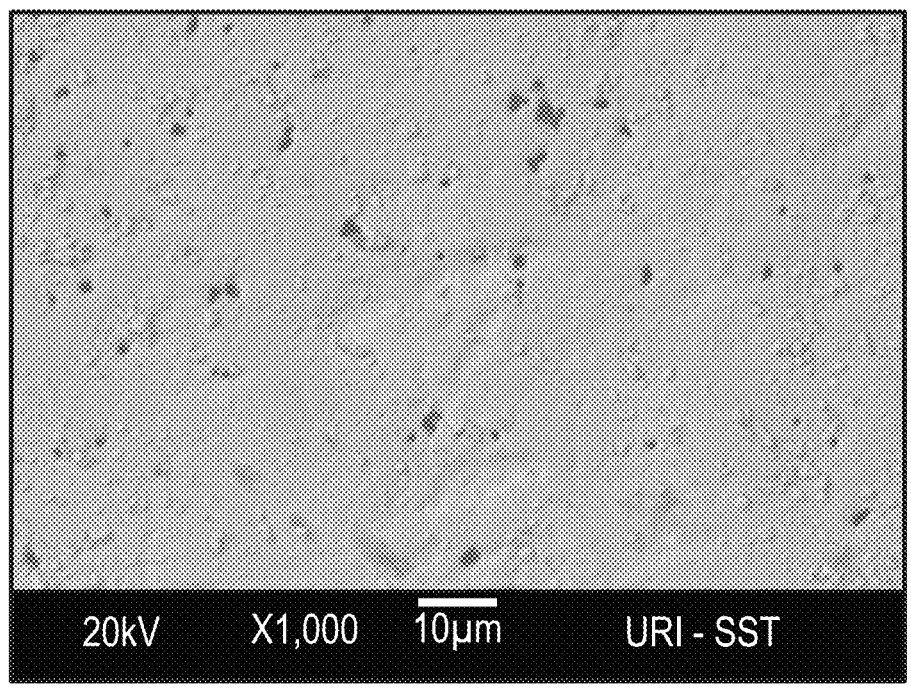
FIG. 24B shows an SEM micrograph of thin-film Pd deposited on the aerogel substrate surface.
Figure 24C:
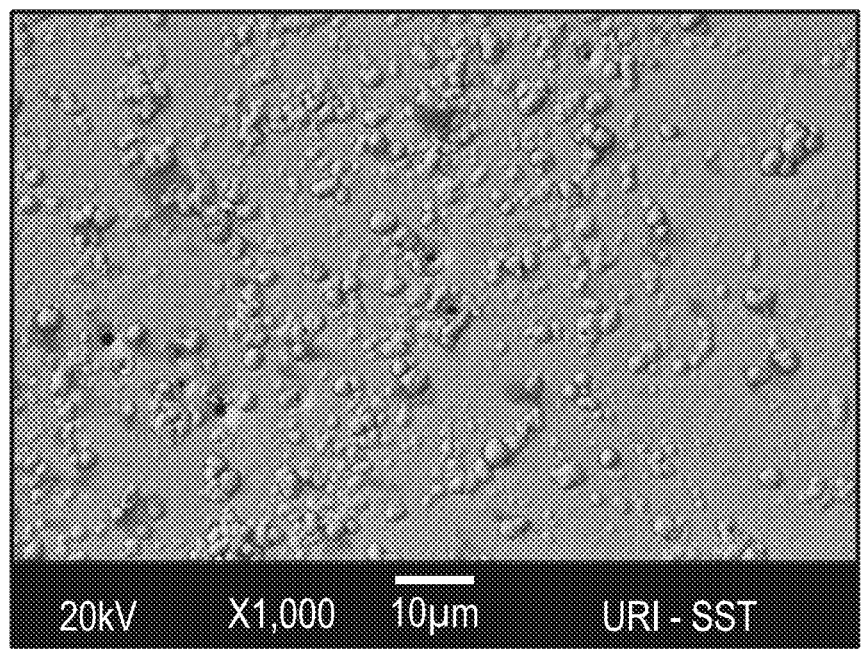
FIG. 24C shows an SEM micrograph of thin-film catalyst deposited on the aerogel substrate surface.

FIG. 24A depicts an SEM micrograph of the aerogel substrate surface. FIG. 24B depicts the same aerogel substrate surface coated by a thin-film Pd microheater. FIG. 24C depicts the aerogel substrate surface coated by a thin-film SnO catalyst. These figures provide context to the above-mentioned findings that the flexible aerogel-based sensor exhibits a greater sensor response. The aerogel substrate surface is shown to be preferably porous resulting in trapped air pockets within the substrate. This trapped air results in an overall thermal conductivity (4.5 W/mK) which is comparable to that of the YSZ substrate (2.7 W/mK) at a lower thermal mass. Due to the aerogel substrate porosity, the thermal mass is considerably lower than that of the YSZ substrate despite a measurable increase in substrate thickness. This porosity is not shown to effect deposition of the adhesion layer or metal microheater as the films are shown to be sufficiently continuous (FIG. 24B). However, deposition of the catalyst layer overtops the porous aerogel is shown to produce nodules on the surface of the catalyst. These nodules are a product of the heating of air molecules with the aerogel during the process of sputtering resulting in increased catalytic surface area. Thus, the enhanced sensor response of the flexible vapor sensor is attributed to the presence of these nodules.

Figure 25:
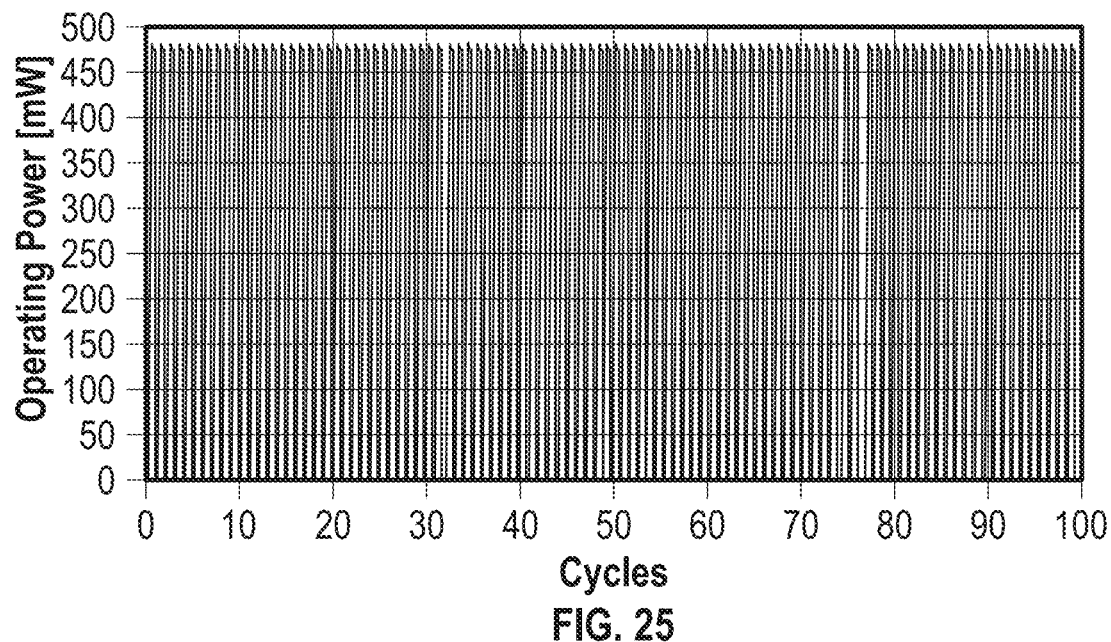
FIG. 25 shows an illustrative graphical representation of the consistency of a flexible vapor sensor during thermal cycling to an operating temperature of 175° C. in 50% relative humidity.

FIG. 25 shows a graphical representation of thermal cycling of a flexible vapor sensor in 50% relative humidity. The aerogel-based microheaters are shown cool to room temperature in just seconds after deactivation, thus making the overall duty cycle much shorter in duration. These features permit real-time detection with little to no delay related to sensor recovery. The flexible vapor sensors also show consistency at the peak operating power in 50% RH representing reproducible performance in real-world conditions. Similarly, the flexible vapor sensors show reproducible responses to vapor phase compounds.

Figure 26:
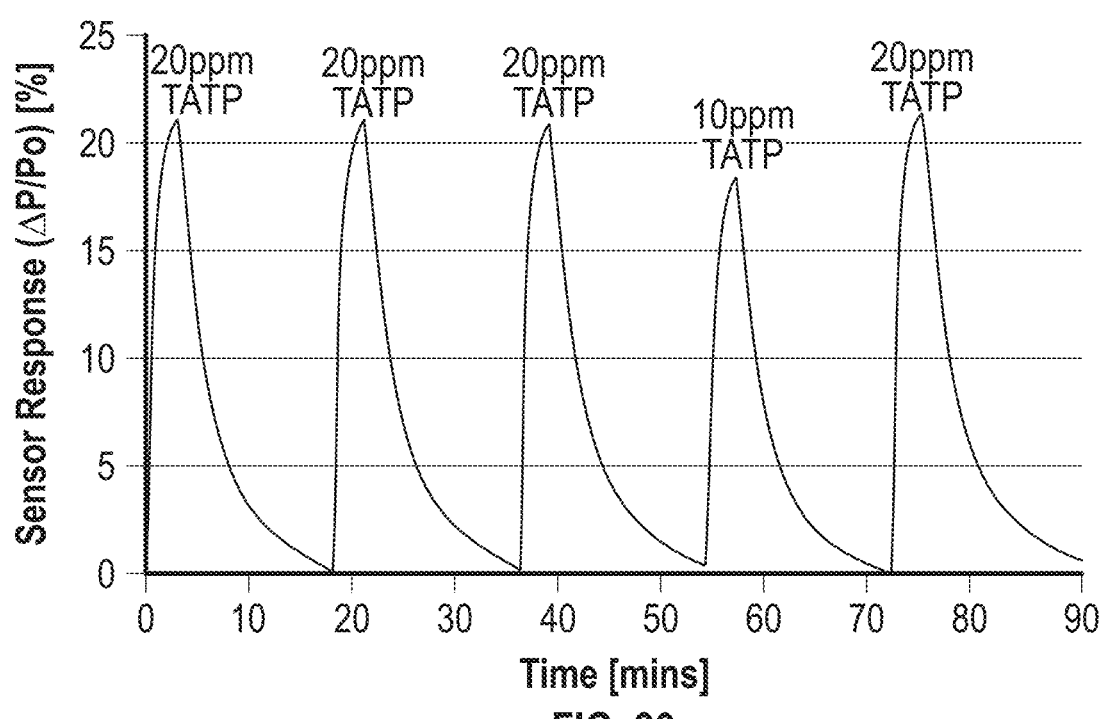
FIG. 26 shows an illustrative graphical representation of the reproducibility of the response of a flexible vapor sensor employing a SnO catalyst to 10 and 20 ppm TATP at an operating temperature of 175° C.

FIG. 26 shows the response of a flexible vapor sensor employing a SnO catalyst at 175° C. to 2 different concentrations of TATP. Here, the flexible vapor sensor shows 3 reproducible responses to 20 ppm TATP before measuring a unique response to 10 ppm TATP. The flexible vapor sensor then displays a response to 20 ppm TATP similar to the response shown before. These results highlight the consistency and reproducibility of the flexible vapor sensor platform.

Figure 27:
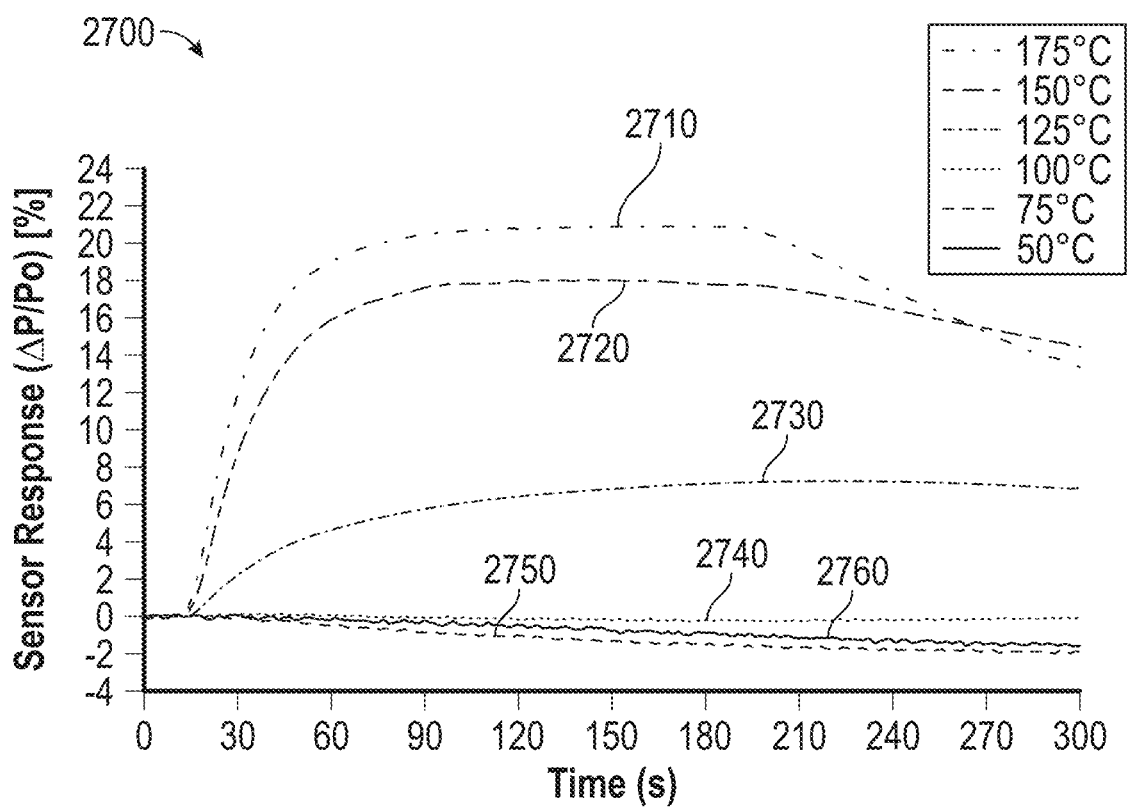
FIG. 27 shows an illustrative graphical representation of a comparison between responses of a flexible vapor sensor employing a SnO catalyst to 20 ppm TATP at a variety of operating temperatures.

FIG. 27 shows comparison 2700 of the responses of a flexible vapor sensor fabricated employing a SnO catalyst to 20 ppm TATP at a variety of temperatures, specifically 175° C. at line 2710, 150° C. at line 2720, 125° C. at line 2730, and 100° C. at line 2740, 75° C. at line 2750, and 50° C. at line 2760. In the embodiment tested, the sensor showed the best overall sensor response to TATP. At a temperature of 175° C., the sensor displayed a sensitivity of 21%, which represents a 40-fold increase in sensitivity over the 40 μm YSZ-based platform. In addition, the aerogel-based substrate promoted greater sensor response at significantly lower operating temperatures. At 50° C., the sensor displayed a sensitivity of around −1.5%, which compares favorably to the other YSZ-based platforms. The significantly lower operating temperatures and electrical power requirements combined with the flexibility of the substrate permits further portability of the sensor platform.

Flexible vapor sensors have also been fabricated employing a variety of other metal oxide catalysts. These include aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO). Each catalyst displays different levels of sensitivity and selectivity based on the chemical reactions that result from the interaction with the target analyte.

Figure 28:
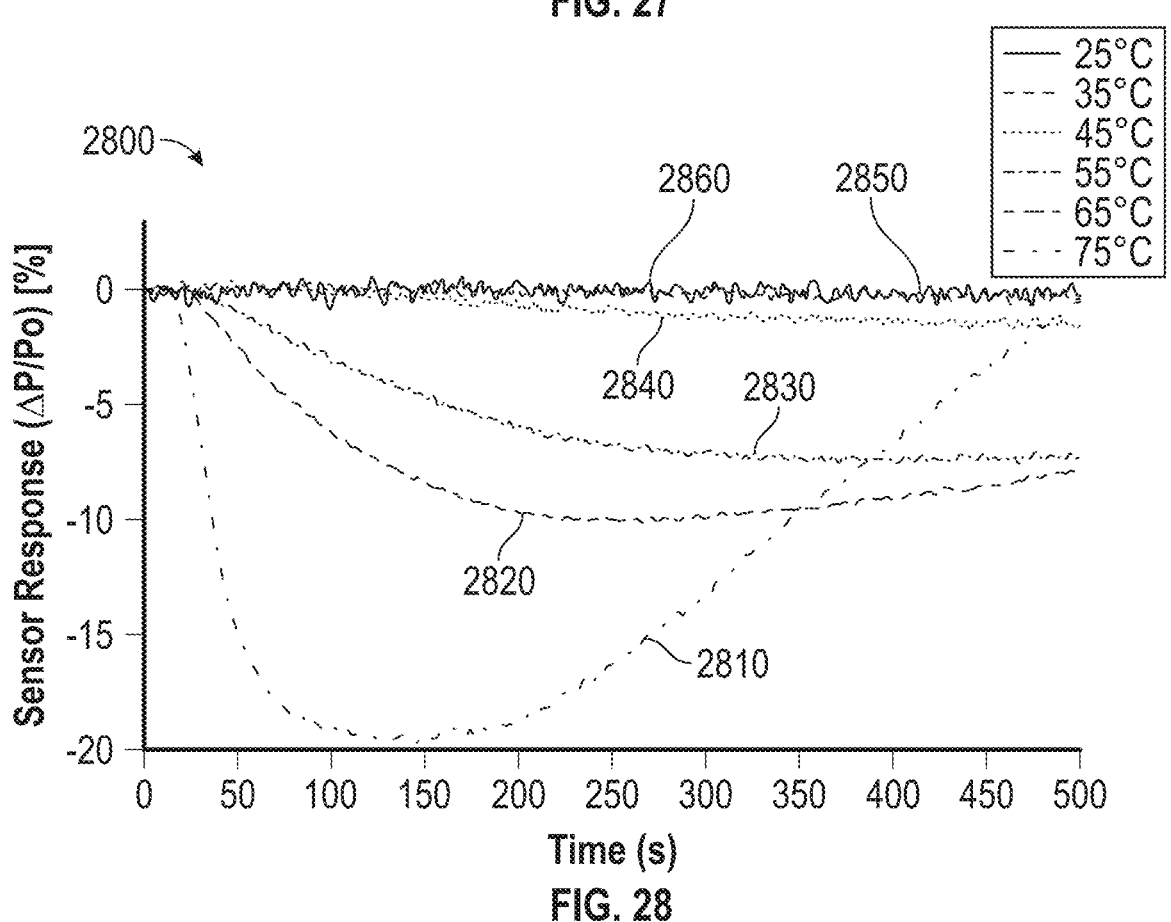
FIG. 28 shows an illustrative graphical representation of a comparison between responses of a flexible vapor sensor employing an ITO catalyst to 20 ppm TATP at a variety of operating temperatures near room temperature.

For example, ITO is a catalyst consisting of highly specific compositions of indium and tin oxide. In reference to FIG. 28, the response of a flexible vapor sensor employing a 1.2 μm thick ITO catalyst to 20 ppm TATP at a variety of operating temperatures near room temperature is described. Specifically, comparison 2800 is made between the flexible vapor sensor at temperatures of 75° C. at line 2810, 65° C. at line 2820, 55° C. at line 2830, 45° C. at line 2840, 35° C. at line 2850, 25° C. at line 2860. At 75° C., the sensor achieved a sensitivity of −20% which represents a 13.5× increase over a similar sensor employing an SnO catalyst. The sensor also shows improved sensitivity at lower operating temperatures. Based on the properties of the catalyst, at operating temperatures less than 100° C., the sensor response is negative, which implies that an exothermic reaction has occurred. These reactions release heat resulting in a decrease in required electrical power and thus, a negative response. At 45° C., the sensor exhibited a −1% response which is an inoperable temperature for a SnO catalyst. This improved sensitivity is a result of ITO's high electrical conductivity, which promotes easy transfer of electrons during oxidation and reduction reactions. Catalysts of this type allow for trace detection at the parts-per-trillion (ppt) level using the flexible vapor sensors. Through room temperature detection, the flexible vapor sensor is uniquely suited to monitoring for vapor compounds onboard a wearable or skin-based platform.

Figure 29:
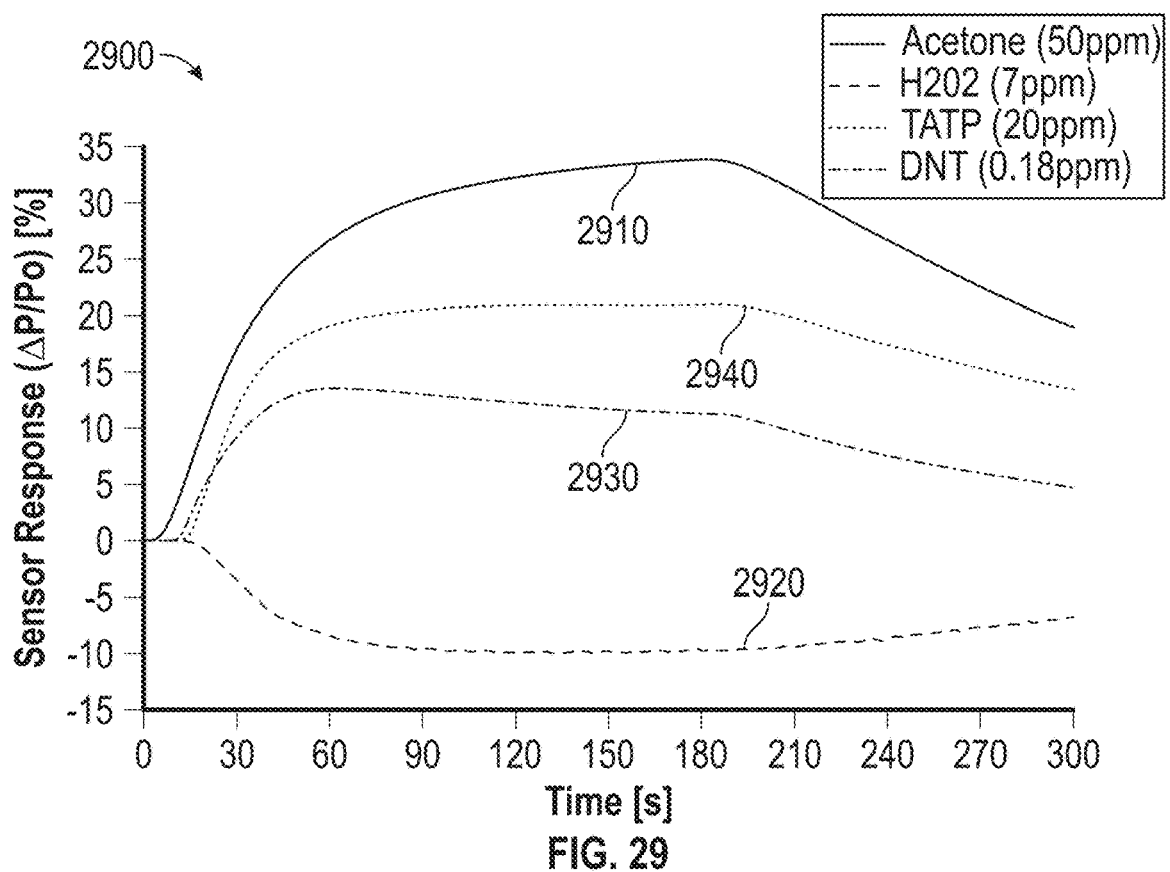
FIG. 29 shows an illustrative graphical representation of a comparison between responses of a flexible vapor sensor employing an SnO catalyst to variety of analytes of different vapor pressures at an operating temperature of 175° C.

In addition to unparalleled sensitivity, the flexible vapor sensor also displays improved selectivity. FIG. 29 shows comparison 2900 of responses of a flexible vapor sensor employing a SnO catalyst to a variety of analytes, including acetone (50 ppm) at line 2910, $H_2O_2$ (7 ppm) at line 2920, 2,4-DNT (0.18 ppm) at line 2930, TATP (20 ppm) at line 2940. Here, the sign and slope of the responses are highly specific toward each analyte. More specifically, flexible vapor sensors employing SnO catalysts exhibited a positive (endothermic response) to acetone, TATP, and 2,4-DNT while also exhibiting a negative (exothermic) response to $H_2O_2$.

Figure 30:
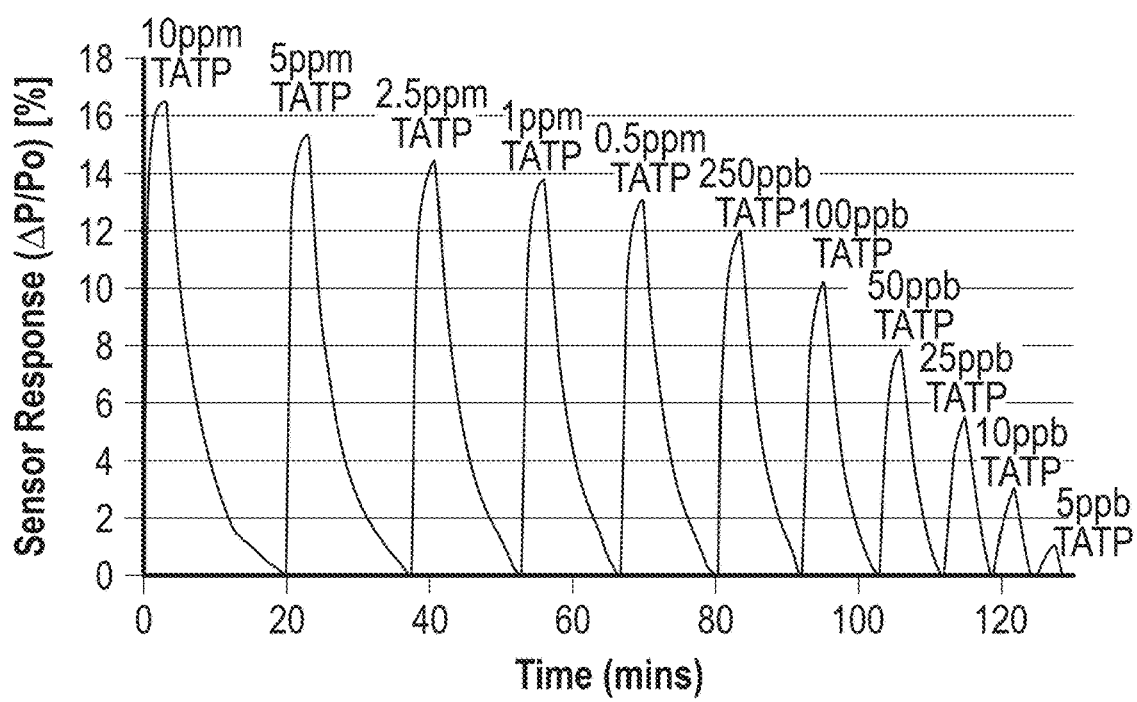
FIG. 30 shows an illustrative graphical representation of the response of a flexible vapor sensor to TATP at a variety of concentrations using an operating temperature of 175° C.

FIG. 30 shows the response of a flexible vapor sensor employing a SnO catalyst at a variety of concentrations at an operating temperature of 175° C. Here, the flexible vapor sensor displays responses at each concentration level with high resolution. Detection was displayed between 10 ppm and 5 ppb which represented the lowest possible dilution level of the sensor testing apparatus. These results represent concentration curves used to correlate the sensor response to analyte concentrations. Thus, concentration curves for either increasing or decreasing concentrations may be generated for the precise measurement of the concentration of a target molecule (or analyte) concentration in the vapor phase.

FIG. 31A and FIG. 31B show a top view of detection device 3100, which may be a flexible vapor sensor, and an exploded view of detection device 3100, respectively. As illustrated in FIG. 31B, detection device 3100 may include multiple layers such as catalyst layer 3110, microheater and adhesion layer 3120, substrate layer 3130, passivation layer 3140, and disposable layer 3150. Detection device 3100 may be designed as a wearable for a subject for detecting existence, identity, and/or concentration of analyte(s), as described herein. Detection device 3100 may have reusable components (e.g., sensor and circuitry portions) and disposable components (components that contact the wearer's skin).

Catalyst layer 3110 is coated with a catalyst selected for detection of a predetermined analyte. The catalyst may be selected to chemically react with the analyte selected for detection. Catalyst layer 3110 may be structured in a similar manner to the catalyst layers described herein, such as catalyst layer 140 described above.

Microheater and adhesion layer 3120 may be formed of metal. Microheater layer 3120 is designed maintain a setpoint temperature via the addition or reduction of heat upon exposure to an endothermic or exothermic chemical reaction, respectively, at catalyst layer 3110. In some embodiments, microheater 3120 is formed using photolithography to pattern a 1-micrometer thick palladium film microheater. Palladium is a preferred choice for the metallization due to its catalytic amplification effect, which has been shown to improve sensitivity and response time. Microheater and adhesion layer 3120 may be structured in a similar manner to the microheater layers and adhesion layers described herein, such as microheater layer 130 and adhesion layer 120, described above.

In preferred embodiments, substrate 3130 is a preferably porous aerogel substrate, which comprises a nominal thickness (e.g., 125 micrometers). Notably, layers of flexible vapor sensor 3100 may have different thicknesses, and the films may be optimized for thickness to maximize surface area of the metal oxide catalyst while still maintaining the low mass characteristics of the microheater. As shown above, the flexible aerogel-based sensor is uniquely suited to detect vapor compounds near room temperatures promoting detection of vapors from the skin.

Passivation layer 3140 may be in contact with substrate layer 3130, microheater and adhesion layer 3120, as illustrated. Passivation layer 3140 may be formed of any material designed to limit heat dissipation (including aerogels, ceramics, or metals). The flexible vapor sensor is capable of detecting compounds at the ppt level at a variety of operating temperatures (25-175° C.). Passivation layer 3140 ensures safe detection of compounds at any temperature by dissipating excess heat away from the skin.

Disposable layer 3150 may be in contact with passivation layer 3140, as illustrated. Disposable layer 3150 may be formed of any material designed to safely interact and adhere to the skin (including bandages, gauze, or stickers).

Microheater and adhesion layer 3120 may be made up of the metallic microheater and the adhesion layer (typically Cu) used to adhere the microheater to substrate layer 3130. Substrate layer 3130 may be adhered to passivation layer 3140 through any high temperature adhesive or epoxy. The adhesive or epoxy can also be used to adhere passivation layer 3140 to the disposable layer 3150.

Detection device 3100 illustratively includes sensor 3160 and reference sensor 3170. Additional sensors beyond 3160 may be included in detection device 3100 similar to the other sensor array configurations described herein.

Detection device 3100 may further include circuitry 3180 that incorporates control and/or power components, such as programmable controller 155, power supply 180, communication circuitry 185, I/O 190, and/or user interface 195, described above with respect to FIG. 1C. Circuitry 3180 may be coupled to, or integrated with, passivation layer 3140 or may be on a secondary device (e.g., another wearable) that is coupled to the sensors (e.g., via leadout wires).

Detection device 3100 may be designed as a specialized flexible vapor sensor for the monitoring of vapor from the skin. This detection device can be designed for a variety of wearable applications including public safety or healthcare. In one embodiment, detection device 3100 may be designed as a wearable sensor capable of operating at higher temperatures (175° C.) for first responders (firefighters, police, etc.) and those tasked with identifying explosive ordinance. In a second embodiment, detection device 3100 may be designed as a wearable sensor capable of monitoring for health biomarkers emanating from the skin. For example, hydrogen peroxide ($H_2O_2$) acts as messenger in wound healing and is present at low concentrations (100-250 μM or ~6 ppm) in normal wounds. Peroxide concentration above this threshold can cause biofilm-making pathogens to grow resulting in infection. Thus, a flexible vapor sensor capable of identification and measurement of hydrogen peroxide is vital for wound monitoring applications.

In reference to FIG. 32, the response of a flexible vapor sensor employing a 1.2 μm thick ITO catalyst to 7 ppm $H_2O_2$ at a variety of operating temperatures near room temperature is described. Specifically, comparison 3200 is made between the flexible vapor sensor at temperatures of 75° C. at line 3210, 65° C. at line 3220, 55° C. at line 3230, 45° C. at line 3240, 35° C. at line 3250, 25° C. at line 3260. At 25° C., the sensor achieved a sensitivity of 0.5% which is unachievable using a YSZ-based vapor sensor. Here, the flexible vapor sensor is shown to be sufficiently sensitive for hydrogen peroxide concentrations comparable to those required for would monitoring applications. Additionally, detection at 25° C. promotes skin-safe implementation of the flexible vapor sensor platform onboard wearable detection device 3100.

Figure 33:
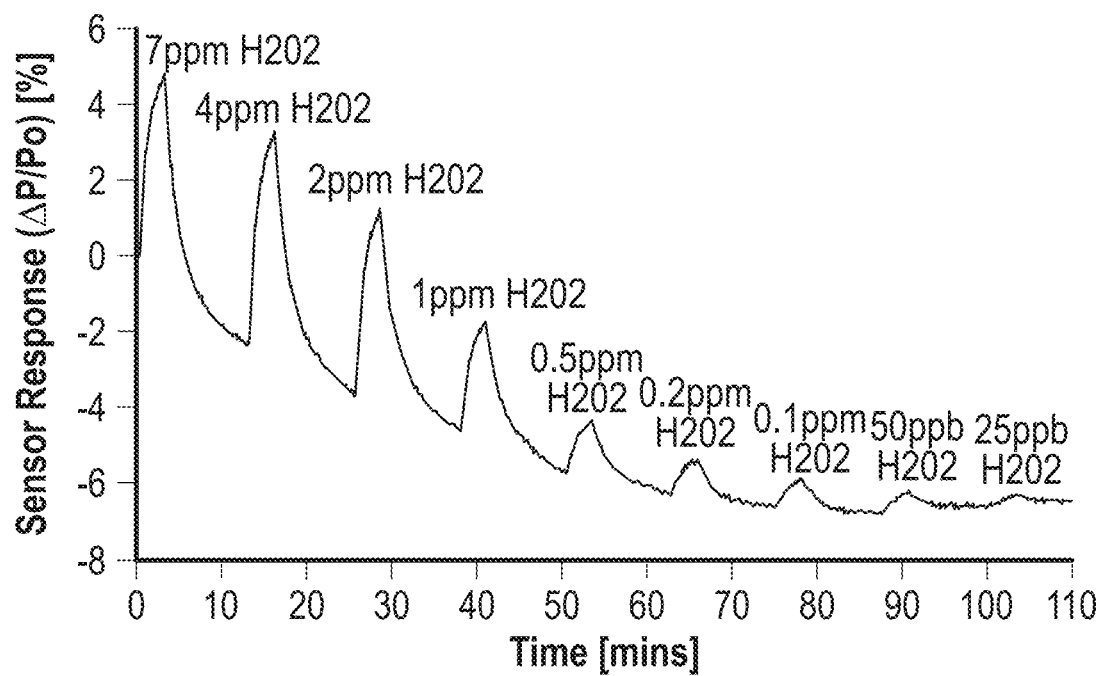
FIG. 33 shows an illustrative graphical representation of the response of a flexible vapor sensor to $H_2O_2$ at a variety of concentrations using an operating temperature of 75° C.

FIG. 33 shows the response of a flexible vapor sensor employing an ITO catalyst at a variety of concentrations at an operating temperature of 55° C. Here, the flexible vapor sensor displays responses at each concentration level with high resolution. Detection was displayed between 7 ppm and 25 ppb which represented the lowest possible dilution level of the sensor testing apparatus. These results represent concentration curves used to calibrate the sensor response to analyte concentrations for wound monitoring applications. Thus, concentration curves for either increasing or decreasing concentrations may be generated for the precise measurement of the concentration of a target molecule (or analyte) concentration in the vapor phase.

Figure 34:
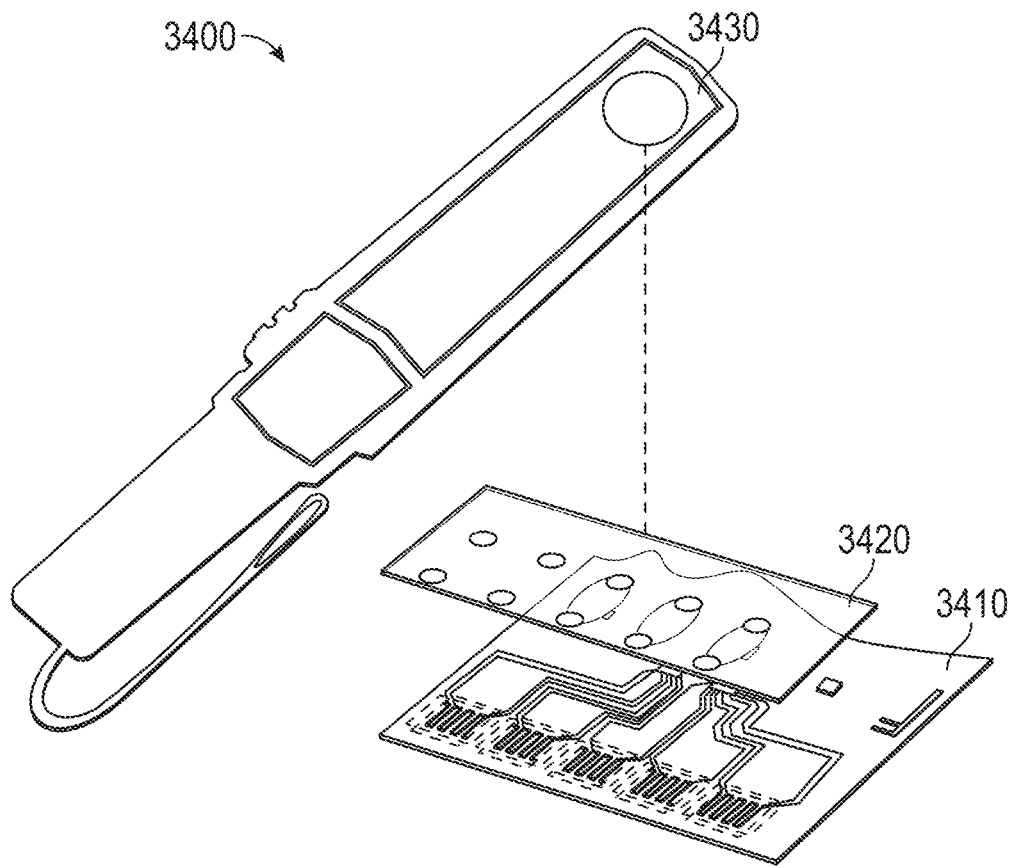
FIG. 34 shows an illustrative representation of an embodiment of a detection device for scanning wand applications.

FIG. 34 shows an illustrative representation of detection device 3400, which may be an ultrathin vapor sensor array employed on a scanning wand. As illustrated in FIG. 34, detection device 3400 may include multiple layers such as sensing layer 3410, laminar flow manifold layer 3420, and scanning device layer 3430.

Sensing layer 3410 possesses an array of ultrathin vapor sensors sharing a common substrate. Each sensor is coated with a catalyst selected for detection of a predetermined analyte. The catalyst may be selected to chemically react with the analyte selected for detection. Each sensor also possesses a microheater designed to maintain a setpoint temperature via the addition or reduction of heat upon exposure to an analyte, depending on whether the chemical reaction is endothermic or exothermic. In some embodiments, the microheaters is formed using photolithography to pattern a 1-micrometer thick palladium film microheater. Palladium is a preferred choice for the metallization due to its catalytic amplification effect, which has been shown to improve sensitivity and response time. In preferred embodiments, the substrate of sensing layer 3410 is an ultrathin YSZ substrate, which comprises a nominal thickness of 20 micrometers. Notably, layers of ultrathin vapor sensor 100 may have different thicknesses, and the films may be optimized for thickness to maximize surface area of the metal oxide catalyst while still maintaining the low mass characteristics of the microheater. Sensing layer 3410 may be structured like any sensor array described herein.

Laminar flow manifold layer 3420 may be in contact with the scanning device layer 3430, and sensing layer 3410, as illustrated. Laminar flow manifold layer 3420 may be formed of any material capable of precision machining (including aerogels, ceramics, or metals). Laminar flow manifold layer 3410 possesses precisely machined throughputs capable of controlling the flow regime of the incoming vapor to ensure laminar flow. The throughputs are designed to provide stable flowrates across each sensor element and allow for efficient ventilation post-detection.

Scanning device layer 3430 may be in contact with laminar flow manifold layer 3420, as illustrated. Scanning device layer 3430 may take the form of any device designed to safely interrogate the airspace around a person, personal belongings, or group of people.

Detection device 3400 may be designed as a specialized vapor sensor array for the monitoring explosives or other "soft targets" as part of a scanning wand platform. This detection device can be designed for a variety of portable applications including public safety. In one embodiment, detection device 3400 may be designed as a portable scanning tool for high throughput scanning of a person, personal belongings or a group of people. The sensor array can be carried by a wand extending from the sensors in order to "sniff" clothing and personal belongings for explosives and other "soft targets." An embodiment of this type could be used by first responders and those tasked with protecting the public at airports, train stations, subway, warzone, government buildings, schools, shipping malls, stadiums, etc., and other densely populated venues.

The sensing systems and methods described herein may utilize structures and methods described in U.S. patent application Ser. No. 17/453,620 to Ricci, entitled "Decoupled Thermodynamic Sensing System," the entire contents of which are incorporated herein by reference.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed:

1. A detection device comprising:
   a first sensor comprising a first microheater and a first catalyst in contact with the first microheater;
   a second sensor comprising a second microheater;
   a controller in electrical communication with the first sensor and the second sensor, the controller configured to:
   cause power to be provided to the first and second sensors to heat the first sensor to a first setpoint temperature and to heat the second sensor to a second setpoint temperature;
   vary power applied to the first sensor and/or the second sensor to account for a thermal response caused by reactions between an analyte and the first catalyst to maintain the first setpoint temperature and the second setpoint temperature; and determine an existence, identity, and/or concentration of the analyte based on the varied the power.

2. The detection device of claim 1, wherein the first setpoint temperature is the same as the second setpoint temperature.

3. The detection device of claim 1, wherein the second sensor is a reference sensor without a catalyst, the reference sensor in electrical communication with the controller.

4. The detection device of claim 1, wherein the second sensor comprises a second catalyst in thermal communication with the second microheater.

5. The detection device of claim 4, further comprising a third sensor comprising a third microheater and a third catalyst in thermal communication with the third microheater, a fourth sensor comprising a fourth microheater and a fourth catalyst in thermal communication with the fourth microheater, and a fifth sensor comprising a fifth microheater and a fifth catalyst in thermal communication with the fifth microheater.

6. The detection device of claim 5, wherein the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO).

7. The detection device of claim 6, further comprising a sixth sensor comprising a sixth catalyst selected from copper oxide (CuO) or manganese oxide (MnO).

8. The detection device of claim 5, wherein the first catalyst, the second catalyst, the third catalyst, the fourth catalyst, and the fifth catalyst each comprise aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

9. The detection device of claim 1, wherein the setpoint temperature is between 25° C. and 175° C.

10. The detection device of claim 1, wherein the first sensor comprises a substrate layer formed from yttria-stabilized-zirconia.

11. The detection device of claim 1, wherein the first sensor comprises a substrate layer formed from aerogel.

12. The detection device of claim 1, wherein the first sensor further comprises an adhesion layer in contact with the substrate layer.

13. The detection device of claim 1, wherein the detection device is incorporated in a wearable configured to be worn by a user.

14. The detection device of claim 13, further comprising a disposable layer configured to be adhered to the user's skin.

15. The detection device of claim 14, further comprising a passivation layer between the disposable layer and the first and second sensors.

16. The detection device of claim 1, wherein the detection device is incorporated in a scanning wand.

17. A method of detecting an analyte, the method comprising:
providing a sensor array comprising a first sensor and a second sensor, the first sensor comprising a first microheater layer and a first catalyst layer in contact with the first microheater layer, the second sensor comprising a second microheater layer;
delivering power to the first and second sensors to heat the first sensor to a first setpoint temperature and to heat the second sensor to a second setpoint temperature;
exposing the first and second sensors to an analyte such that the first catalyst layer reacts with the analyte to generate a thermal response;
varying power applied to the first sensor and/or the second sensor to account for the thermal response to maintain the first setpoint temperature and the second setpoint temperature; and
determining an existence, identity, and/or concentration of the analyte based on varying the power.

18. The method of claim 17, wherein the first setpoint temperature and the second setpoint temperature are each between 25° C. and 175° C.

19. A detection device comprising:
a substrate layer;
a microheater layer configured to receive power at a first power level to reach a setpoint temperature; and
a catalyst layer in contact with the microheater layer, the catalyst layer comprising a catalyst configured to undergo a chemical reaction when exposed to an analyte, the chemical reaction being endothermic or exothermic,
wherein the microheater layer is configured to receive power at a second power level to maintain the setpoint temperature after the catalyst begins the chemical reaction, and
wherein a heat effect indicative of information on the analyte is determined by comparing the second power level to the first power level.

20. The detection device of claim 19, further comprising an adhesion layer in contact with the substrate layer and in contact with the microheater layer.

21. The detection device of claim 19, wherein the substrate is aerogel.

* * * * *